(12) United States Patent
Scheib et al.

(10) Patent No.: US 11,751,870 B2
(45) Date of Patent: Sep. 12, 2023

(54) ARTICULATION DRIVE FEATURES FOR SURGICAL STAPLER

(71) Applicant: Cilag GmbH International, Zug (CH)

(72) Inventors: Charles J. Scheib, Loveland, OH (US); John C. Schuckmann, Cicinnati, OH (US); Jeffrey C. Gagel, Loveland, OH (US); Jason M. Rector, Maineville, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/573,685

(22) Filed: Jan. 12, 2022

(65) Prior Publication Data

US 2022/0192659 A1    Jun. 23, 2022

Related U.S. Application Data

(60) Continuation of application No. 16/372,496, filed on Apr. 2, 2019, now Pat. No. 11,234,696, which is a
(Continued)

(51) Int. Cl.
*A61B 17/064* (2006.01)
*A61B 17/068* (2006.01)
(Continued)

(52) U.S. Cl.
CPC ........ *A61B 17/0686* (2013.01); *A61B 17/068* (2013.01); *A61B 17/07207* (2013.01); *A61B 17/07292* (2013.01); *A61B 17/29* (2013.01); *A61B 17/2909* (2013.01); *A61B 50/30* (2016.02); *A61B 2017/00017* (2013.01); *A61B 2017/0023* (2013.01); *A61B 2017/0046* (2013.01); *A61B 2017/00327* (2013.01);
(Continued)

(58) Field of Classification Search
CPC ........ A61B 17/068; A61B 2017/00367; A61B 2017/2927; A61B 2017/2929
USPC ............................................ 227/175.1–182.1
See application file for complete search history.

(56) References Cited

U.S. PATENT DOCUMENTS 5,423,471 A * 6/1995 Mastri ................. A61B 17/068
227/181.1
8,485,413 B2 * 7/2013 Scheib ............. A61B 17/07207
227/176.1
(Continued)

*Primary Examiner* — Eyamindae C Jallow
(74) *Attorney, Agent, or Firm* — Frost Brown Todd LLP

(57) ABSTRACT

An apparatus comprises a shaft, an end effector, an articulation joint, and an articulation drive assembly. The shaft has a longitudinal axis. The end effector is operable to staple tissue. The articulation joint couples the shaft with the end effector. The end effector is pivotable at the articulation joint to selectively deflect the end effector away from the longitudinal axis of the shaft. The articulation drive assembly is operable to pivot the end effector at the articulation joint. The articulation drive assembly comprises a first link and a second link. The first link is longitudinally translatable relative to the shaft assembly. The distal end of the first link is pivotably coupled with the proximal end of the second link. The distal end of the second link is pivotably coupled with the end effector. The articulation drive assembly articulates the end effector in response to longitudinal translation of the first link.

20 Claims, 36 Drawing Sheets

Related U.S. Application Data division of application No. 14/314,125, filed on Jun. 25, 2014, now Pat. No. 10,292,701.

(51) Int. Cl.
  *A61B 17/072* (2006.01)
  *A61B 17/29* (2006.01)
  *A61B 17/00* (2006.01)
  *A61B 50/30* (2016.01)
  *A61B 90/00* (2016.01)

(52) U.S. Cl.
  CPC ........... *A61B 2017/00389* (2013.01); *A61B 2017/00424* (2013.01); *A61B 2017/00734* (2013.01); *A61B 2017/2923* (2013.01); *A61B 2017/2927* (2013.01); *A61B 2017/2946* (2013.01); *A61B 2050/314* (2016.02); *A61B 2090/0814* (2016.02)

(56) References Cited

U.S. PATENT DOCUMENTS

| | | | |
|---|---|---|---|
| 8,899,462 B2* | 12/2014 | Kostrzewski | A61B 17/07207 227/176.1 |
| 2009/0188965 A1* | 7/2009 | Levin | A61B 17/068 606/213 |
| 2010/0193566 A1* | 8/2010 | Scheib | A61B 17/07207 227/180.1 |
| 2015/0073439 A1* | 3/2015 | Dannaher | A61B 17/1285 606/142 |
| 2016/0106510 A1* | 4/2016 | Burbank | A61B 34/71 606/130 |
| 2016/0174971 A1* | 6/2016 | Baxter, III | A61B 17/105 227/176.1 |
| 2016/0174976 A1* | 6/2016 | Morgan | A61B 17/07207 227/175.1 |

* cited by examiner

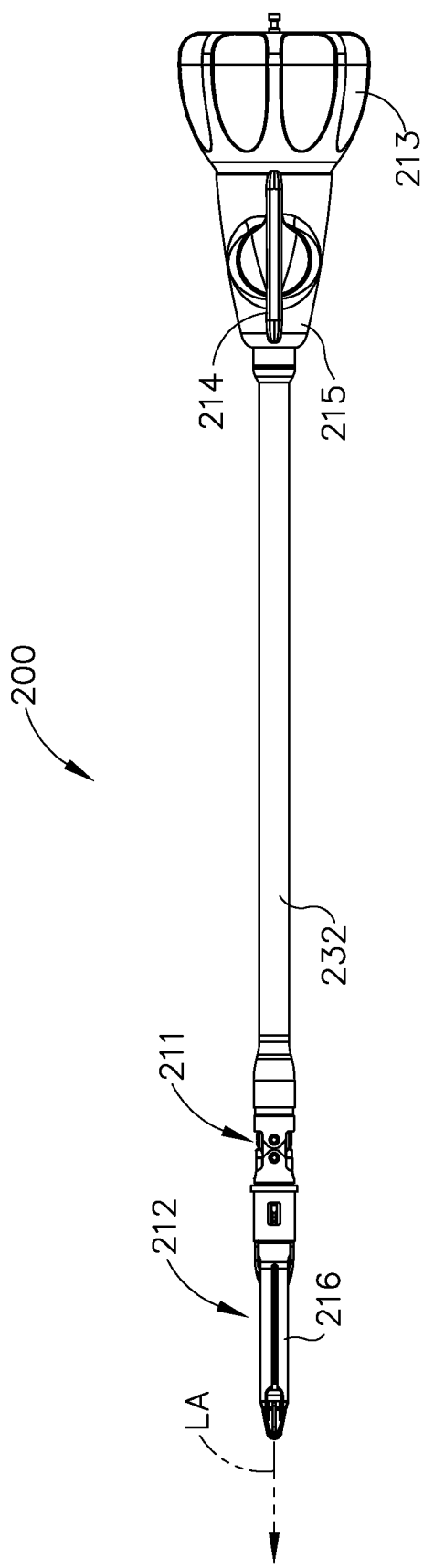

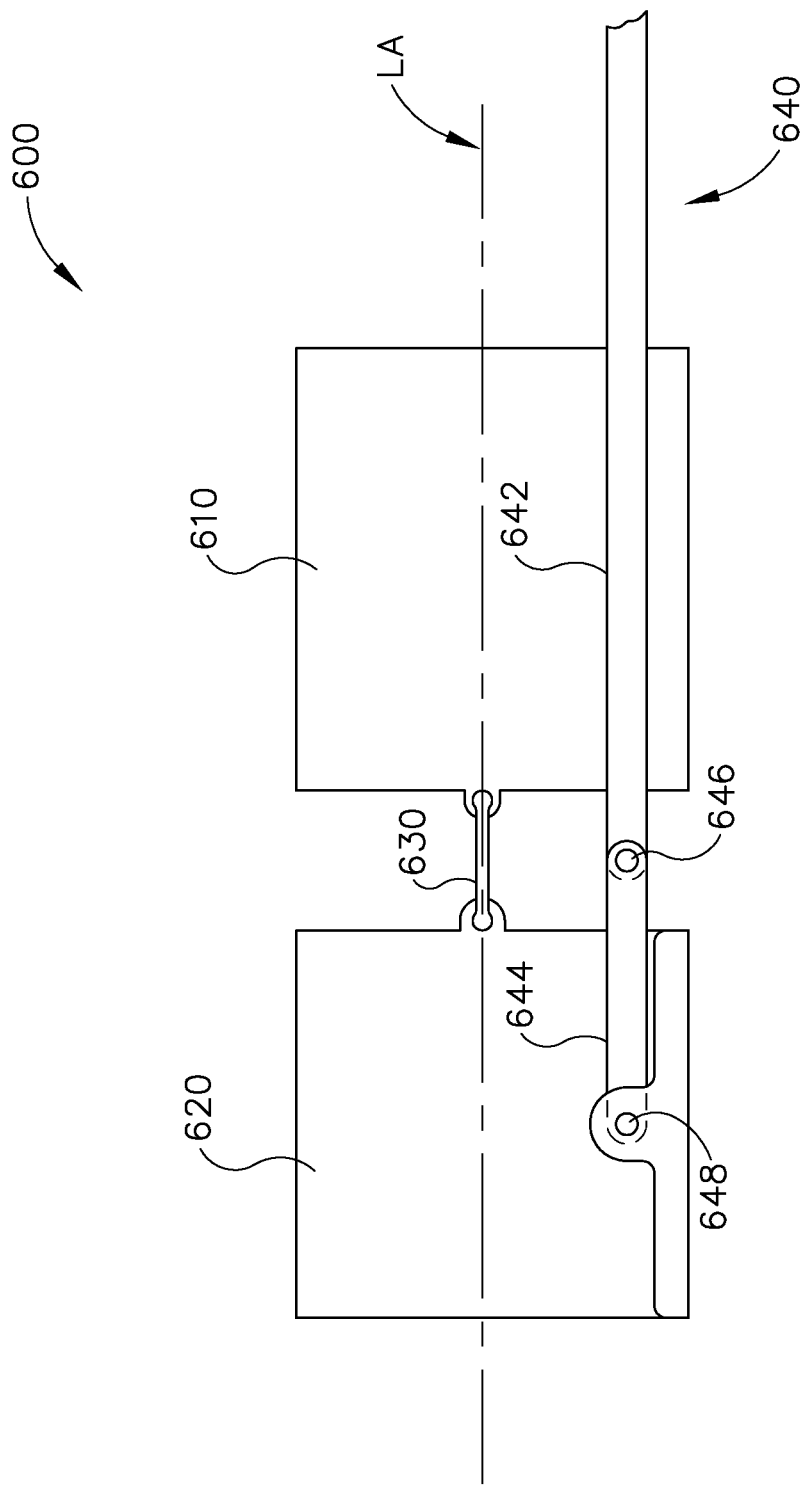

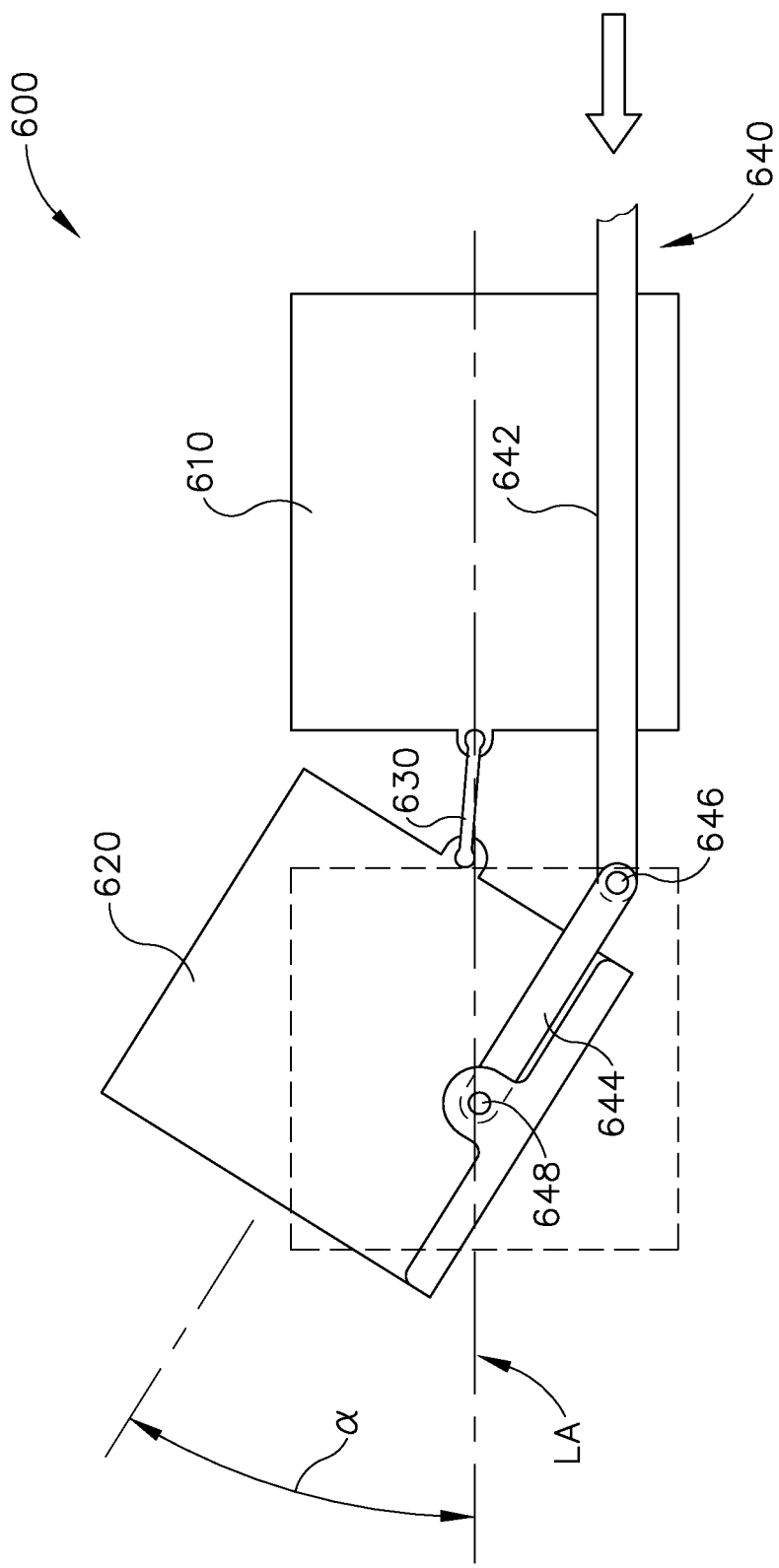

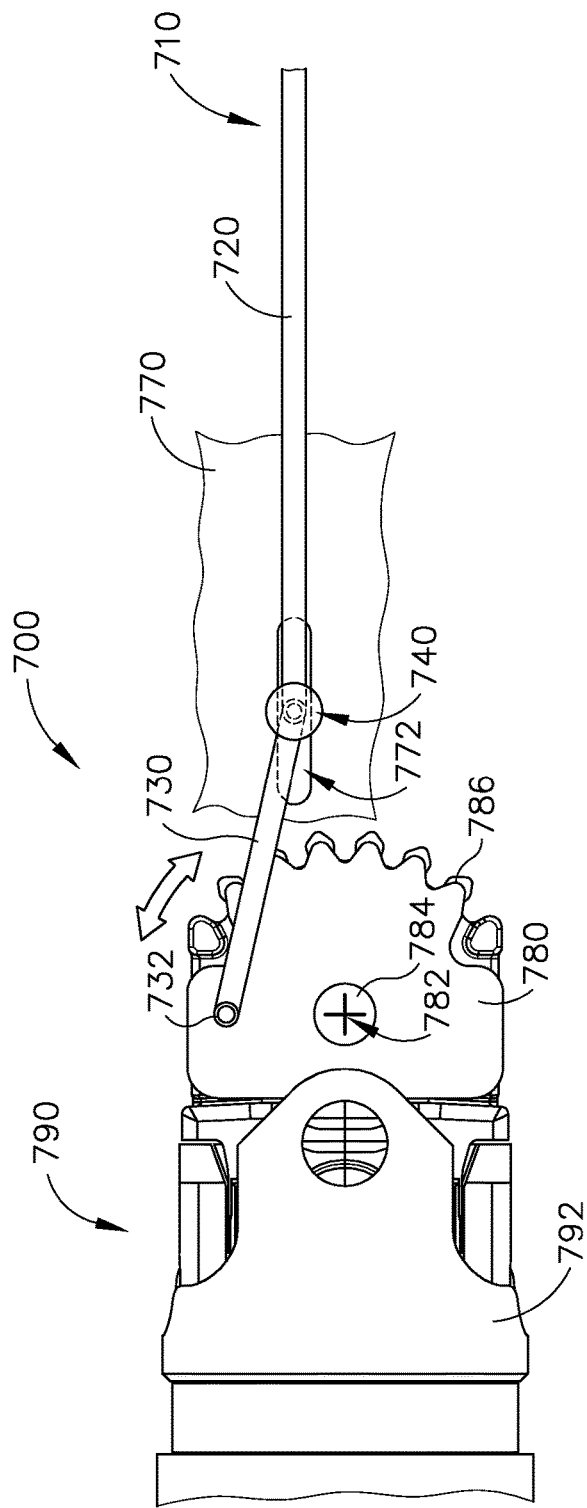
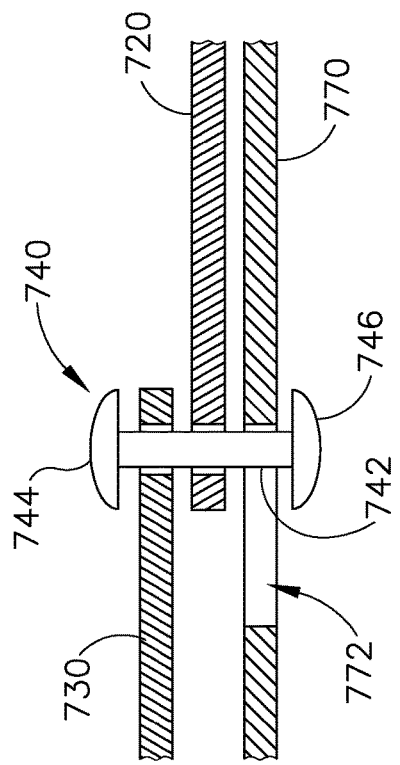
Fig.25
Fig.26

ARTICULATION DRIVE FEATURES FOR SURGICAL STAPLER

This application is a continuation of U.S. patent application Ser. No. 16/372,496, entitled "Articulation Drive Features for Surgical Stapler," filed Apr. 2, 2019, issued as U.S. Pat. No. 11,234,696 on Feb. 1, 2022, which is a divisional of U.S. patent application Ser. No. 14/314,125, entitled "Articulation Drive Features for Surgical Stapler," filed Jun. 25, 2014, issued as U.S. Pat. No. 10,292,701 on May 21, 2019.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015; U.S. patent application Ser. No. 13/780,082, entitled "Lockout Feature for Movable Cutting Member of Surgical Instrument," filed Feb. 28, 2013, issued as U.S. Pat. No. 9,717,497 on Aug. 1, 2017; U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016; U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017; U.S. patent application Ser. No. 13/780,162, entitled "Surgical Instrument with Articulation Lock having a Detenting Binary Spring," filed Feb. 28, 2013, issued as U.S. Pat. No. 9,867,615 on Jan. 16, 2018; U.S. patent application Ser. No. 13/780,171, entitled "Distal Tip Features for End Effector of Surgical Instrument," filed Feb. 28, 2013, issued as U.S. Pat. No. 9,622,746 on Apr. 18, 2017; U.S. patent application Ser. No. 13/780,379, entitled "Staple Forming Features for Surgical Stapling Instrument," filed Feb. 28, 2013, issued as U.S. Pat. No. 10,092,292 on Oct. 9, 2018; U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017; and U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 14A depicts a top, plan view of the shaft assembly of FIG. 13 with the end effector in a first, straight position;

FIG. 24A depicts a partial, top plan view of other exemplary alternative articulation drive features that may be incorporated into the articulation section of the shaft assembly of FIG. 13, with the articulation section in a straight configuration;

FIG. 24B depicts a partial, top plan view of the articulation drive features of FIG. 24A, with the articulation section in a first articulated configuration;

FIG. 25 depicts a partial, top plan view of other exemplary alternative articulation drive features that may be incorporated into the articulation section of the shaft assembly of FIG. 13; and FIG. 26 depicts a partial, cross-sectional side view of some of the articulation drive features of FIG. 25.

Figure 1:
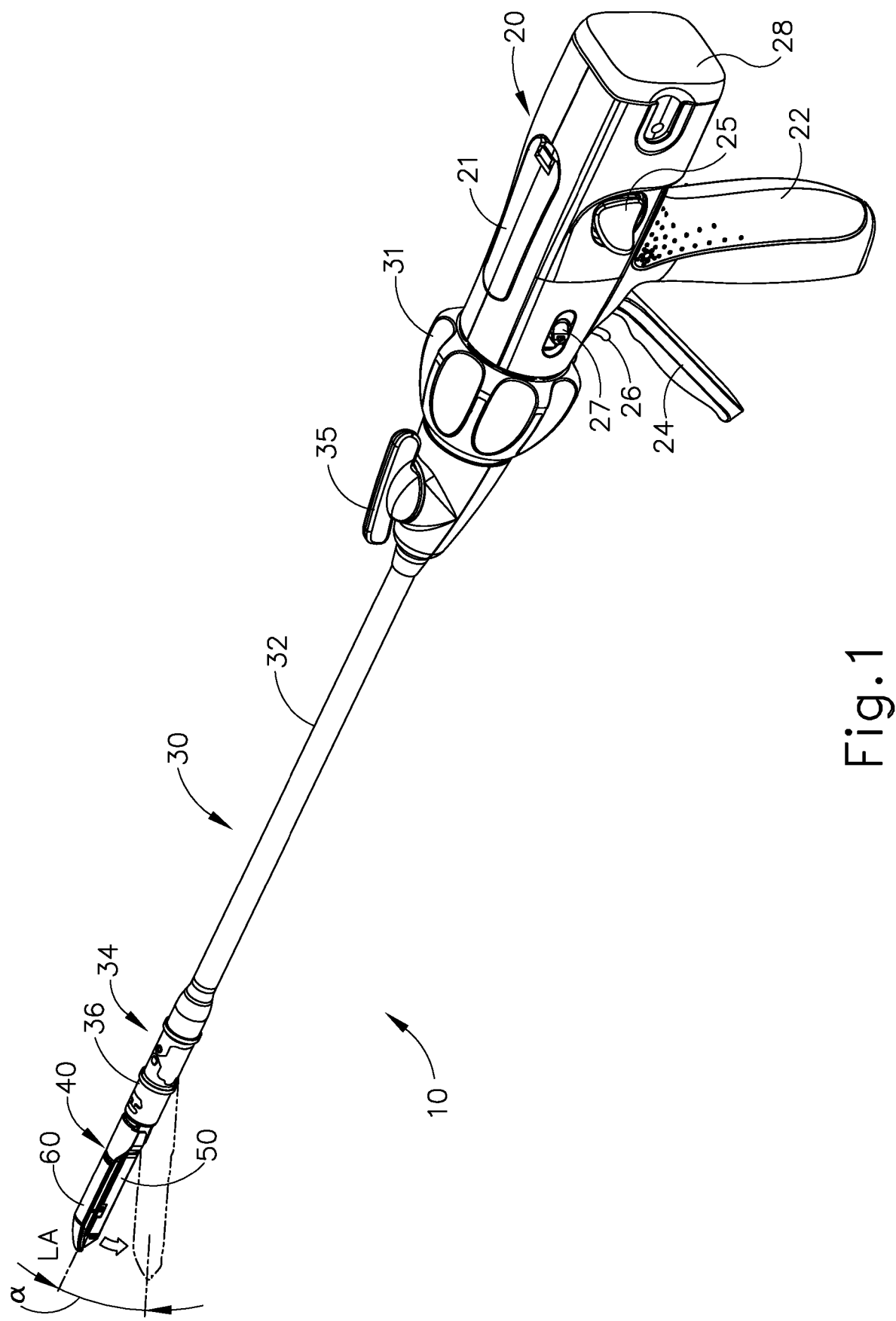
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
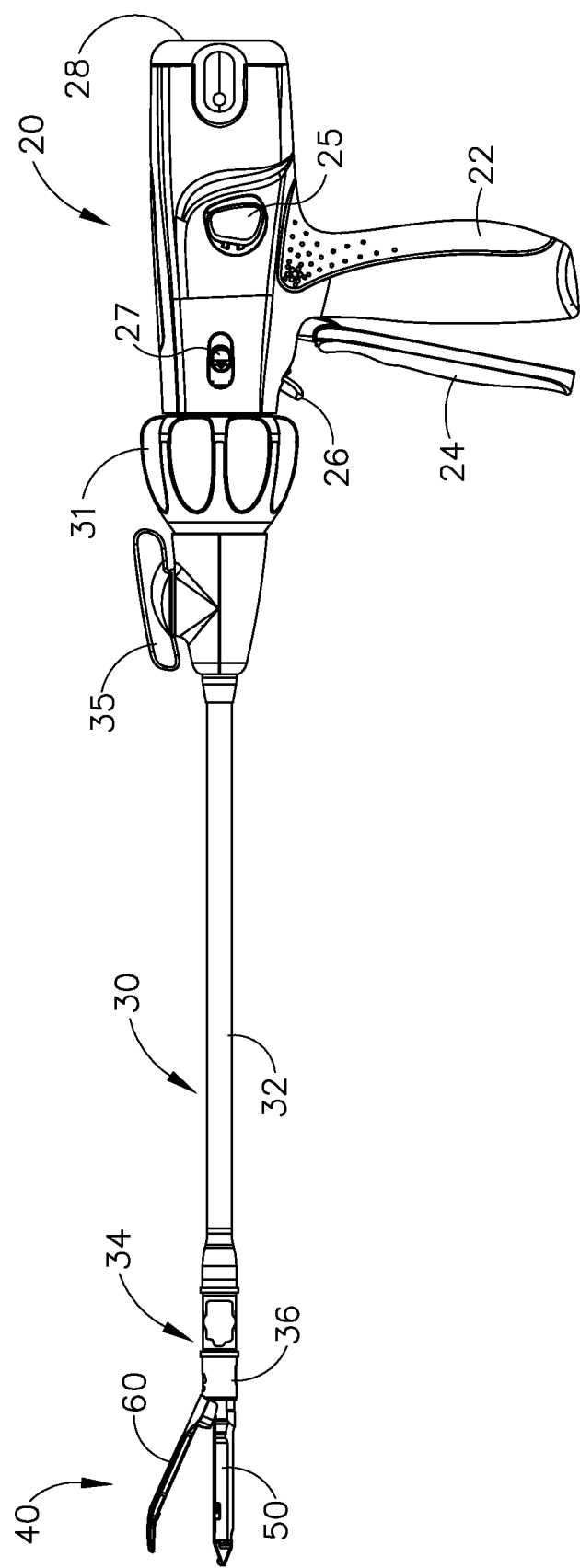
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein. Furthermore, it should be understood that handle assembly (20) is merely an exemplary type of body assembly that can be included within instrument (10) and instrument (10) may comprise any other suitable body assembly in addition to or instead of handle assembly (20), including but not limited to a body assembly configured to allow instrument (10) to be used during robotic-assisted medical treatments and procedures.

Figure 3:
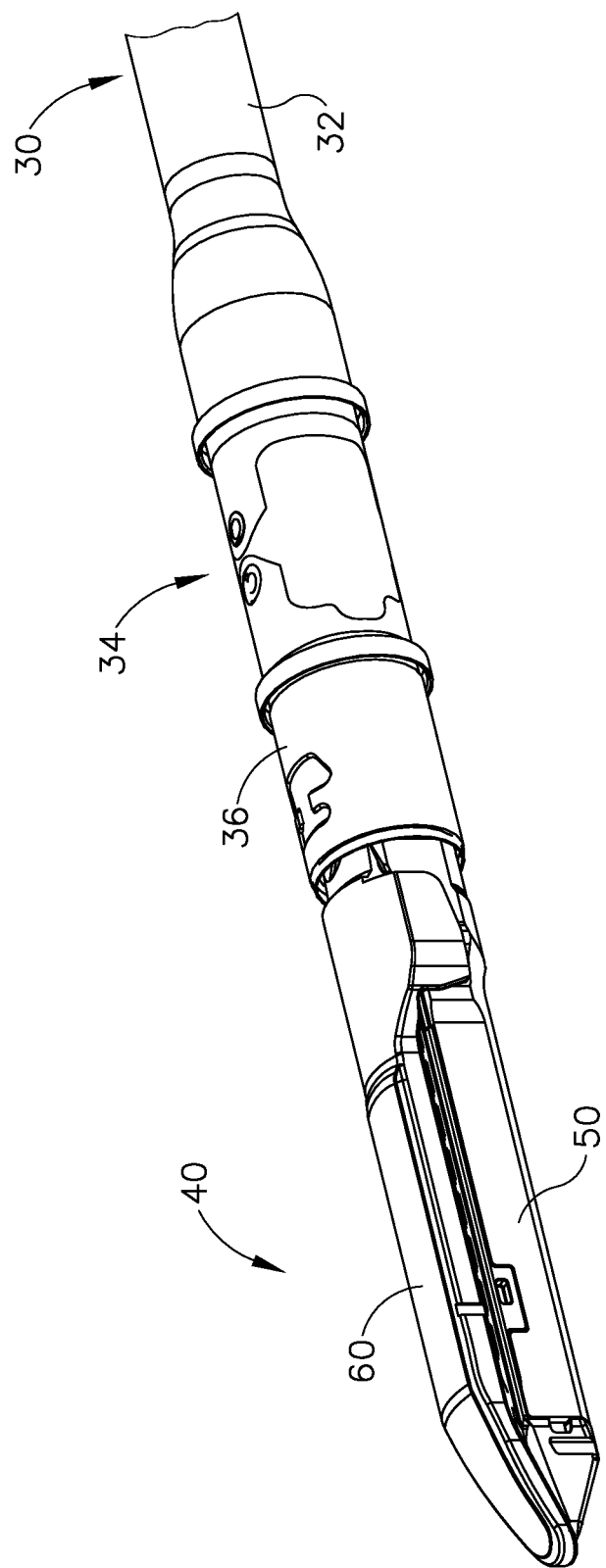
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

It will be appreciated that as a user urges instrument (10) into a surgical region, it may be desirable to approach the tissue to be clamped, stapled, or cut, from a particular angle. For instance, once end effector (40) of instrument (10) is inserted through a trocar, thoracotomy, or other passageway for entering a surgical area, the tissue that the user wishes to target may be positioned out of reach or at an askew angle in relation to end effector (40) that is aligned with closure tube (32). Thus, it may be desirable for portions of instrument (10), such as end effector (40), to articulate such that the user can position end effector (40) to squarely or perpendicularly clamp against a vessel or other tissue. It will further be understood that articulating end effector (40) to squarely position end effector (40) against tissue may promote full seating and clamping of the tissue prior to cutting and stapling tissue. In addition to articulating, it may be desirable for end effector (12) to be selectively locked in a straight or articulated position such that a constant manual bias by the user is not necessary to prevent end effector (12) from pivoting or bending at articulation section (34). It may also be desirable to automatically lock upon articulation, without requiring actuations of a separate articulation locking feature.

Articulation section (34) is operable to laterally deflect closure ring (36) and end effector (40) laterally away from the longitudinal axis (LA) of shaft assembly (30) at a desired angle (α). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015, the disclosure of which is incorporated by reference herein. As yet another merely illustrative example, articulation section (34) may also be constructed and operable in accordance with at least some of the teachings of U.S. patent application Ser. No. 13/780,402, entitled "Surgical Instrument with Articulation Lock Having a Detenting Binary Spring," filed Feb. 28, 2013, issued as U.S. Pat. No. 9,795,379 on Oct. 24, 2017, the disclosure of which is incorporated by reference herein. Articulation section (34) may also be constructed and operable in accordance with at least some of the teachings of U.S. patent application Ser. No. 14/314,276, entitled "Method of Unlocking Articulation Joint in Surgical Stapler," filed Jun. 25, 2014, issued as U.S. Pat. No. 10,064,620 on Sep. 4, 2018, the disclosure of which is incorporated by reference herein; and/or at least some of the teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 4:
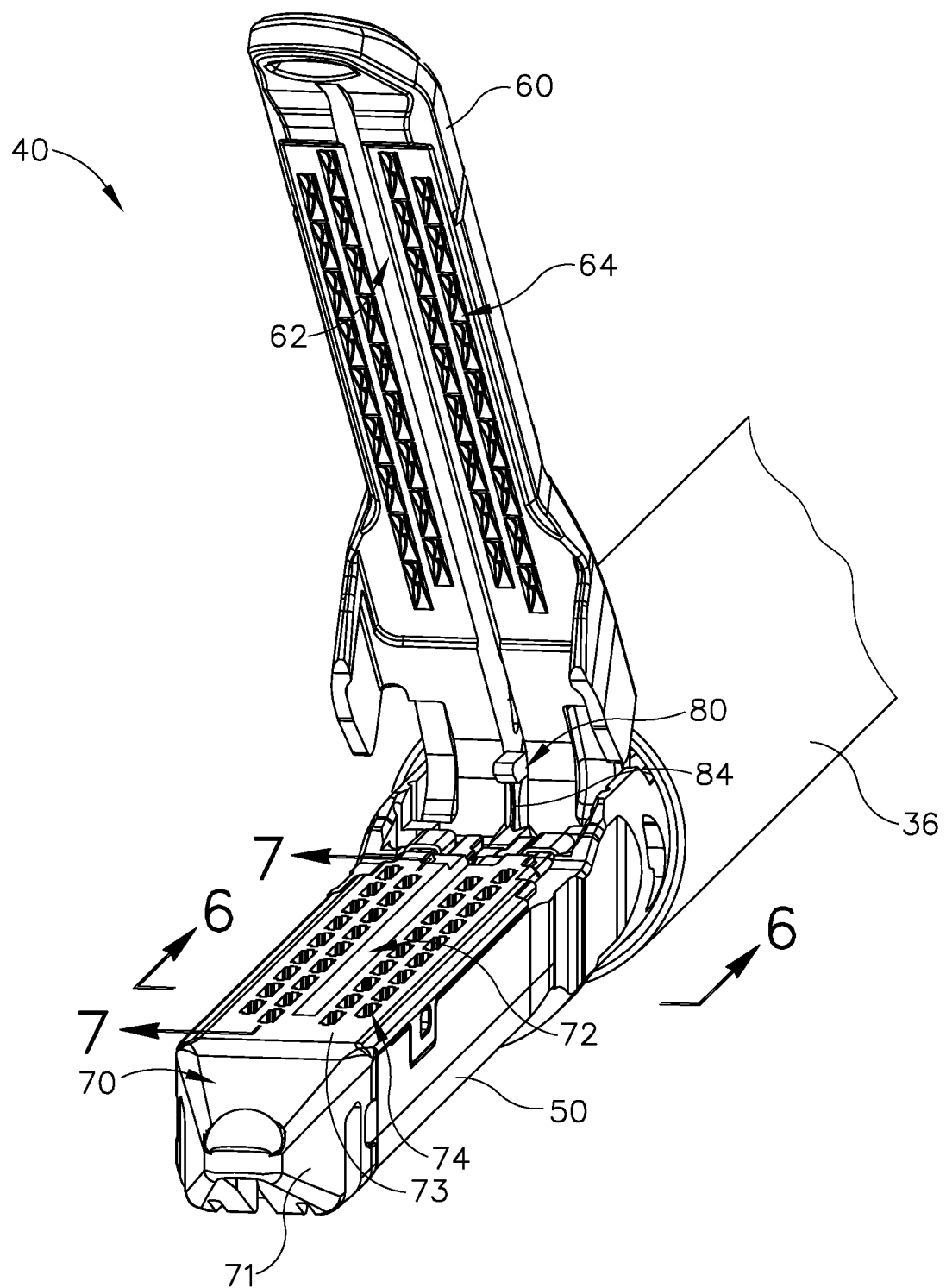
FIG. 4 depicts a perspective view of the end effector of FIG. 3, with the end effector in an open configuration.
Figure 5:
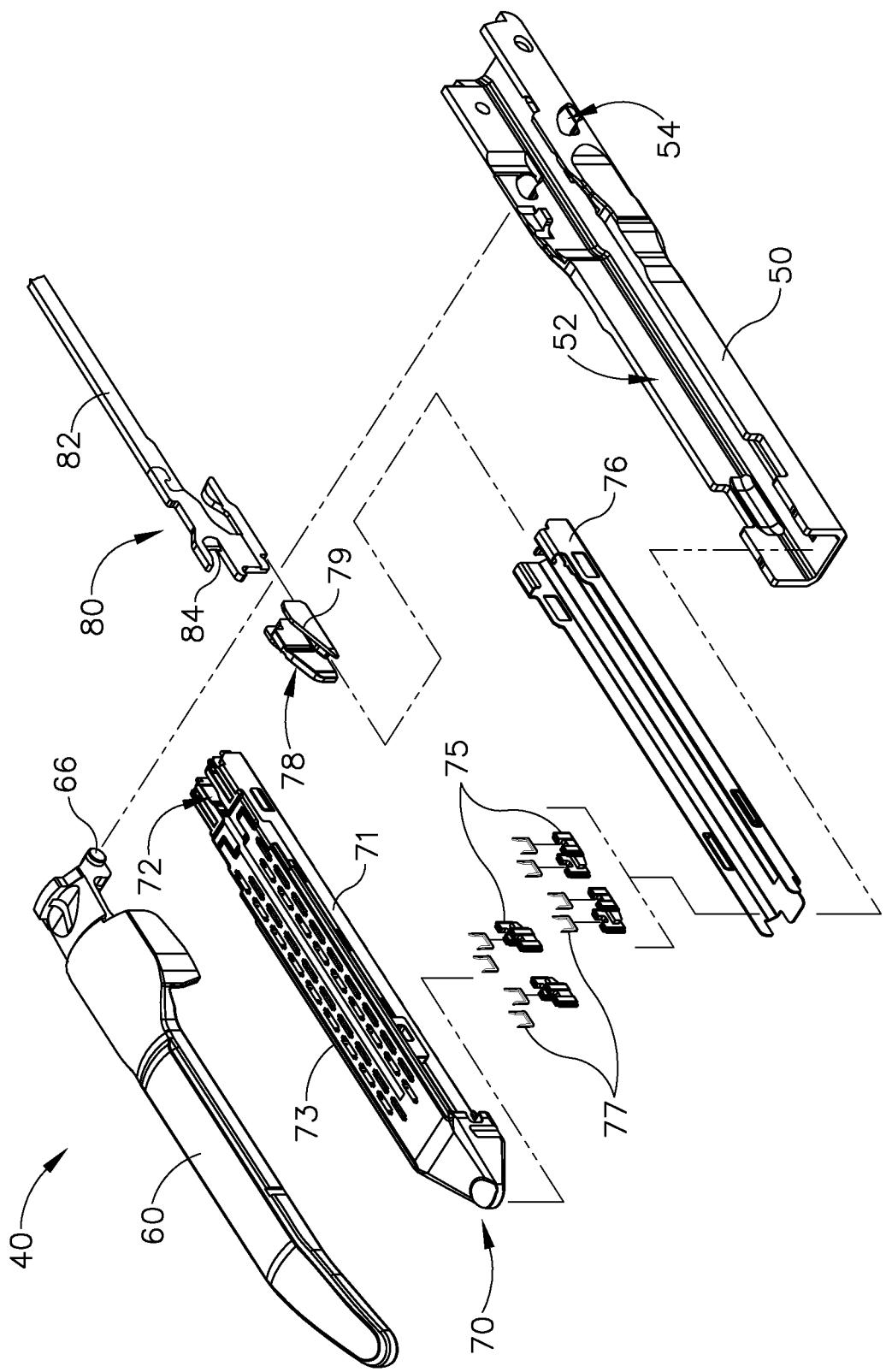
FIG. 5 depicts an exploded perspective view of the end effector of FIG. 3.
Figure 6:
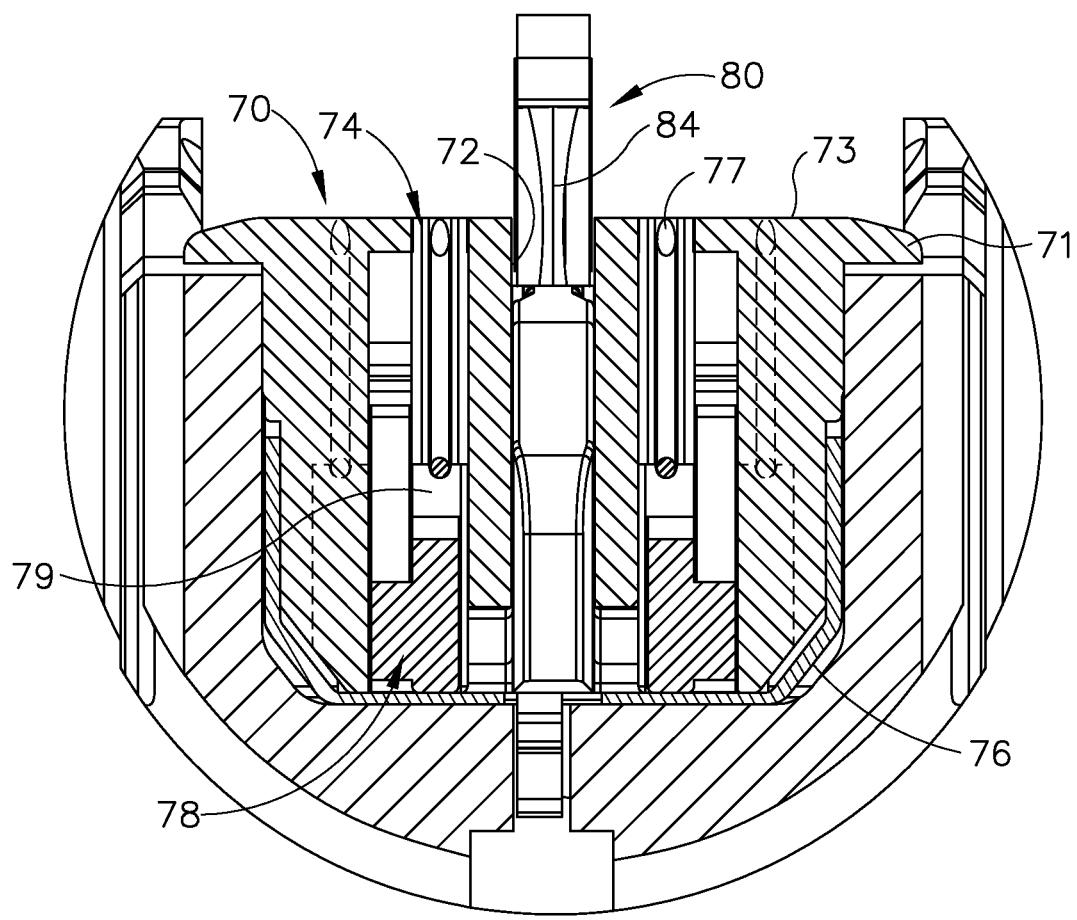
FIG. 6 depicts a cross-sectional end view of the end effector of FIG. 3, taken along line 6-6 of FIG. 4.
Figure 7A:
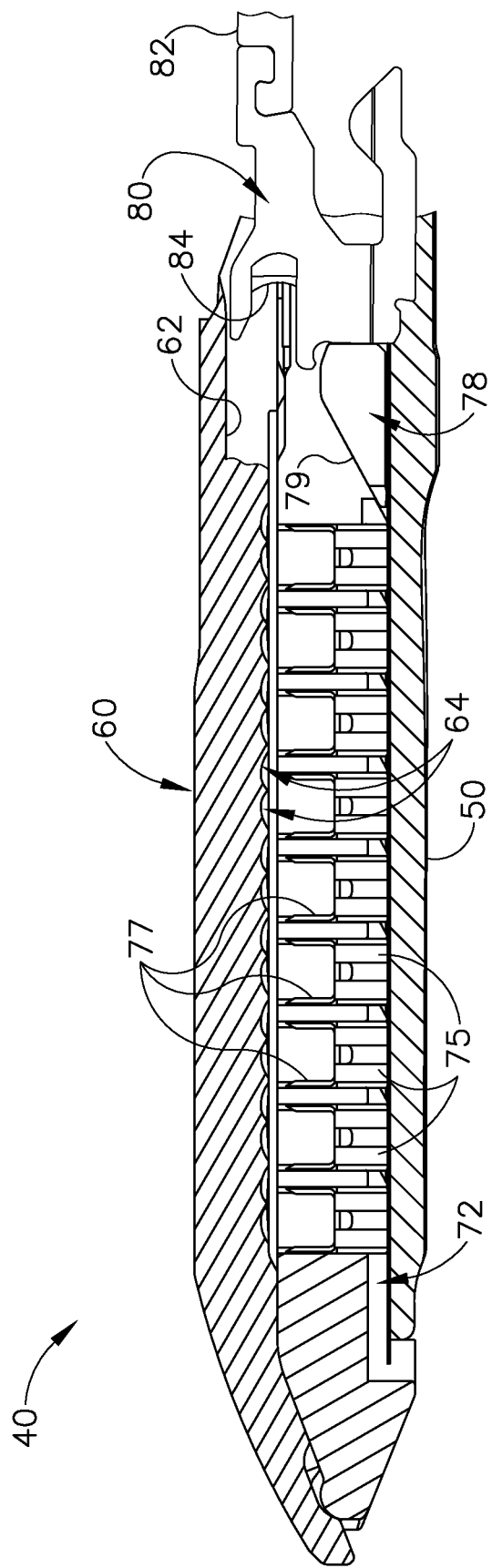
FIG. 7A depicts a cross-sectional side view of the end effector of FIG. 3, taken along line 7-7 of FIG. 4, with the firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016; at least some of the teachings of U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017; and/or at least some of the teachings of U.S. patent application Ser. No. 13/780,379, entitled "Staple Forming Features for Surgical Stapling Instrument," filed Feb. 28, 2013, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
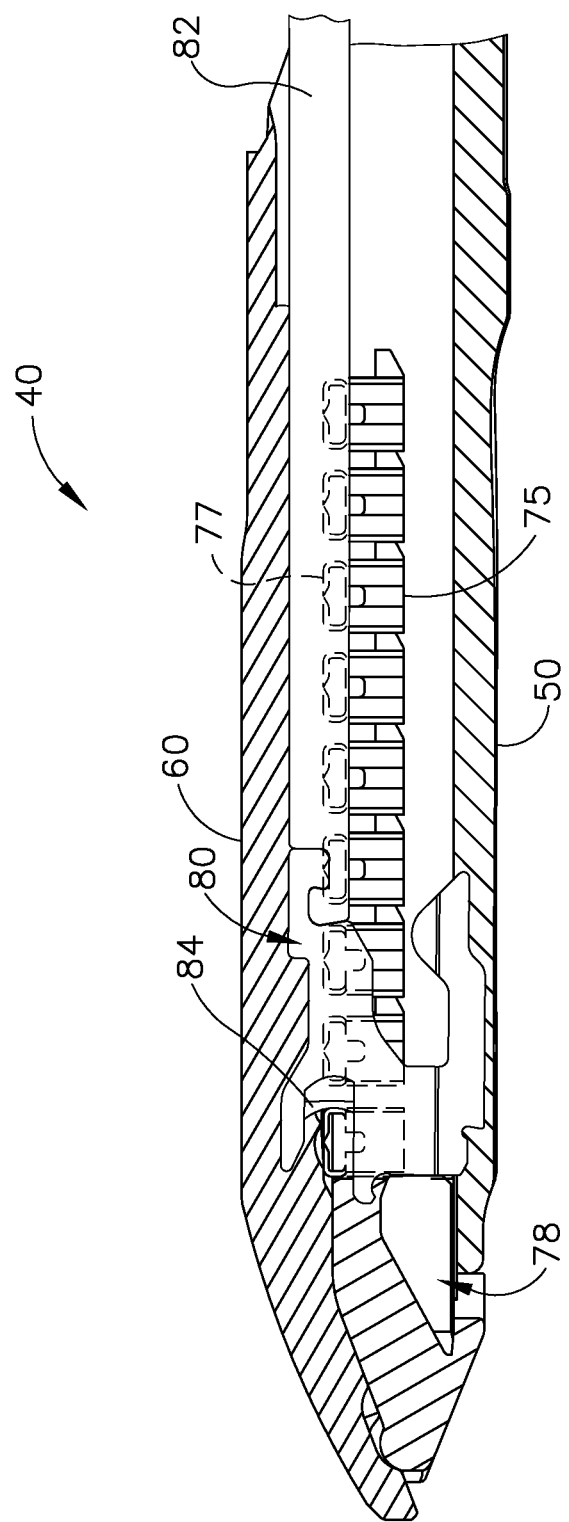
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. patent application Ser. No. 13/780,082, entitled "Lockout Feature for Movable Cutting Member of Surgical Instrument," filed Feb. 28, 2013, issued as U.S. Pat. No. 9,717,497 on Aug. 1, 2017, the disclosure of which is incorporated by reference herein; and/or at least some of the teachings of U.S. patent application Ser. No. 14/314,108, entitled "Method of Using Lockout Features for Surgical Stapler Cartridge," filed Jun. 25, 2014, issued as U.S. Pat. No. 10,335,147 on Jul. 2, 2019, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017, the disclosure of which is incorporated by reference herein; and/or in accordance with at least some of the teachings of U.S. patent application Ser. No. 14/314,164, entitled "Jaw Opening Feature for Surgical Stapler," filed Jun. 25, 2014, issued as U.S. Pat. No. 10,456,132 on Oct. 29, 2019, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

Figure 9:
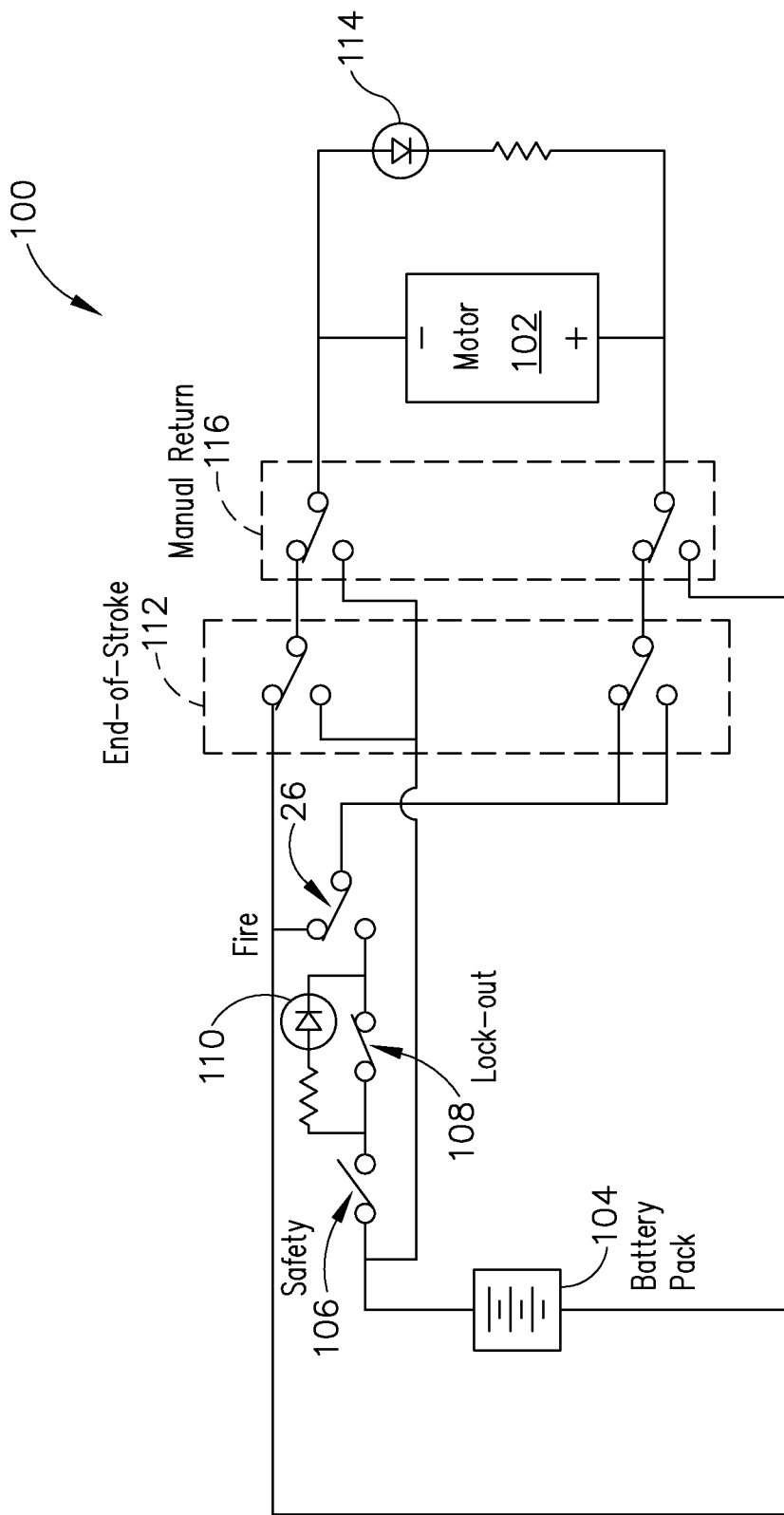
FIG. 9 depicts a schematic view of an exemplary control circuit for use in the instrument of FIG. 1.

In the present example, instrument (10) provides motorized control of firing beam (82). FIGS. 9-12 show exemplary components that may be used to provide motorized control of firing beam (82). In particular, FIG. 9 shows an exemplary control circuit (100) that may be used to power an electric motor (102) with electric power from a battery pack (28) (also shown in FIGS. 1-2). Electric motor (102) is operable to translate firing beam (82) longitudinally as will be described in greater detail below. It should be understood that the entire control circuit (100), including motor (102) and battery pack (28), may be housed within handle assembly (20). FIG. 9 shows firing trigger (26) as an open switch, though it should be understood that this switch is closed when firing trigger (26) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle assembly (20). Safety switch (106) may also provide a mechanical lockout of firing trigger (26), such that firing trigger (26) is mechanically blocked from actuation until safety switch (106) is actuated.

Circuit (100) of the present example also includes a lockout switch (108), which is configured to be closed by default but is automatically opened in response to a lockout condition. By way of example only, a lockout condition may include one or more of the following: the absence of a cartridge (70) in lower jaw (50), the presence of a spent (e.g., previously fired) cartridge (70) in lower jaw (50), an insufficiently closed anvil (60), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Figure 12:
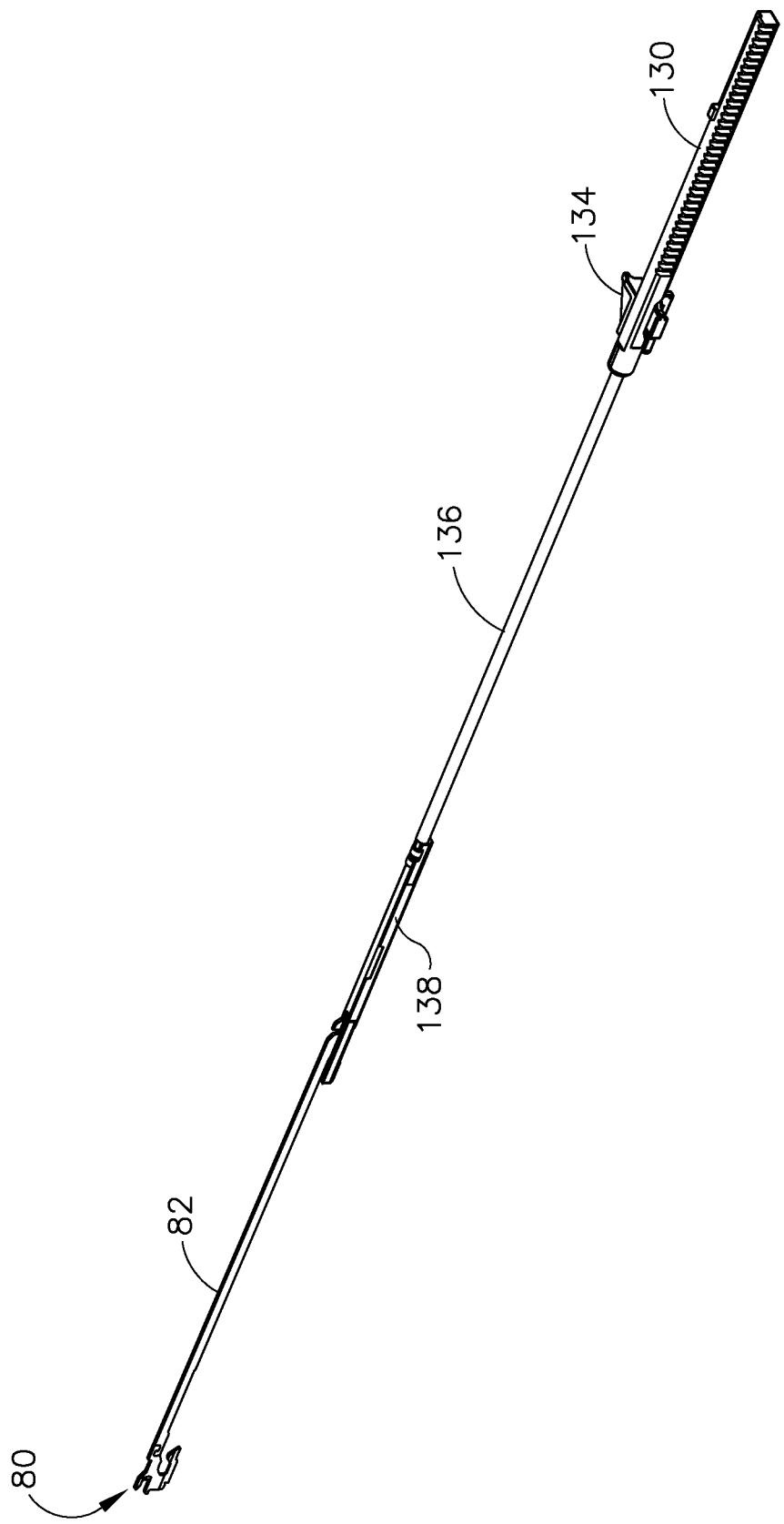
FIG. 12 depicts a perspective view of an elongate member from the drive assembly of FIG. 11, coupled with the firing beam.
Figure 13:
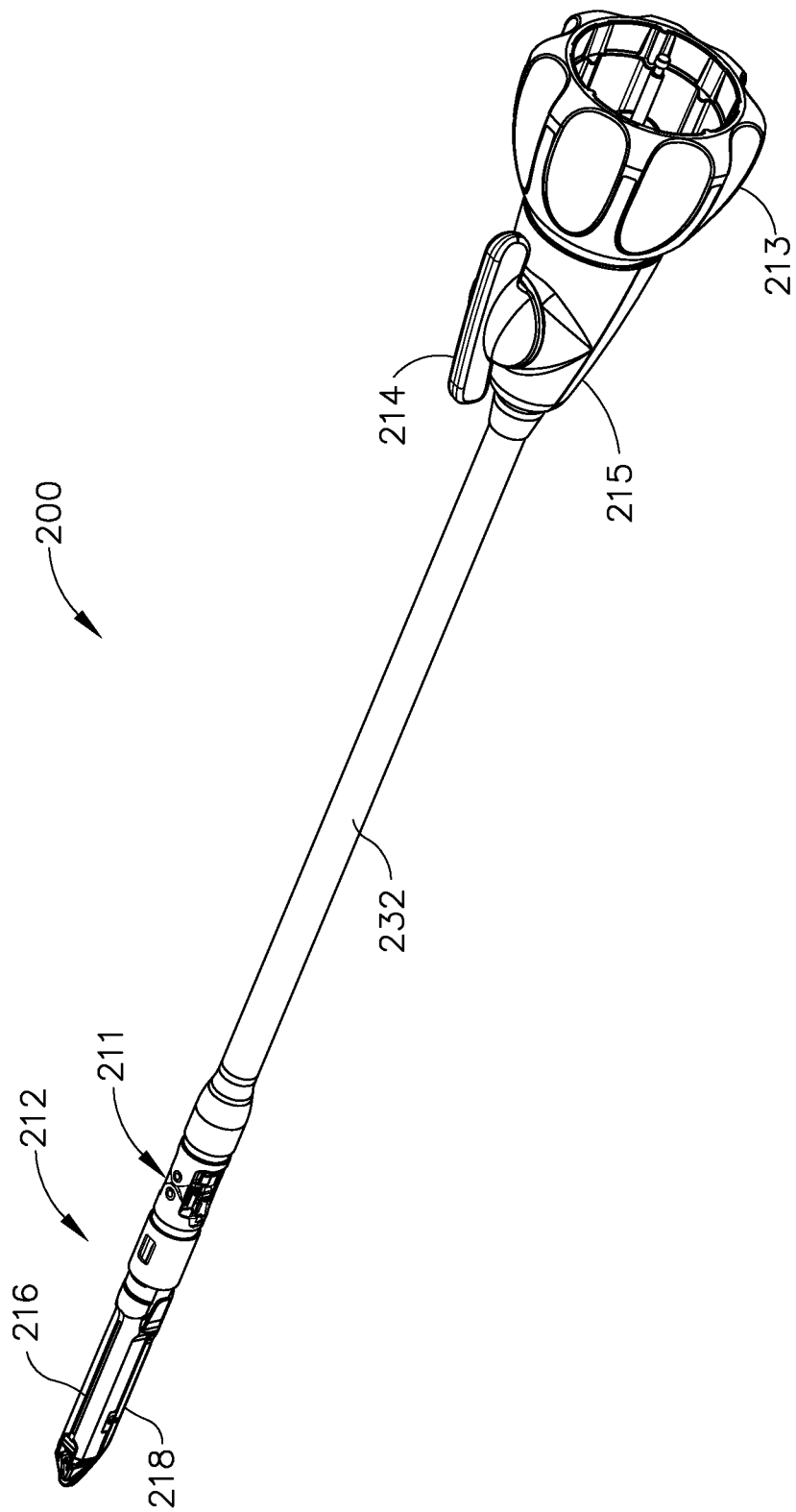
FIG. 13 depicts a top, perspective view of an exemplary alternative shaft assembly that may be incorporated into the instrument of FIG. 1.

Once firing beam (82) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (26) at this stage of operation. In this operational state, current flows through a reverse direction indicator (114) (e.g., an LED, etc.) to provide a visual indication to the operator that motor (102) rotation has been reversed. In the present example, and as best seen in FIG. 12, a switch actuation arm (134) extends laterally from rack member (130), and is positioned to engage end-of-stroke switch (112) when firing beam (82) reaches a distal-most position (e.g., after tissue (90) has been severed and staples (77) have been driven into tissue (90)). Various other suitable ways in which end-of-stroke switch (112) may be automatically switched to a closed position when firing beam (82) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle assembly (20) of the present example also includes a manual return switch (116), which is also shown in circuit (100). In the present example, return switch (116) is activated by actuating reverse switch (27), which is shown on handle assembly (20) in FIG. 1. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114). In some versions, handle assembly (20) further includes a mechanical return feature that enables the operator to manually reverse firing beam (82) and thereby retract firing beam (82) mechanically. In the present example, this manual return feature comprises a lever that is covered by a removable panel (21) as shown in FIG. 1. Manual return switch (116) and the mechanical return feature are each configured to act as a "bailout" feature, enabling the operator to quickly begin retracting firing beam (82) proximally during a firing stroke. In other words, manual return switch (116) or the mechanical return feature may be actuated when firing beam (82) has only been partially advanced distally.

In some versions, one or more of switches (26, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 10:
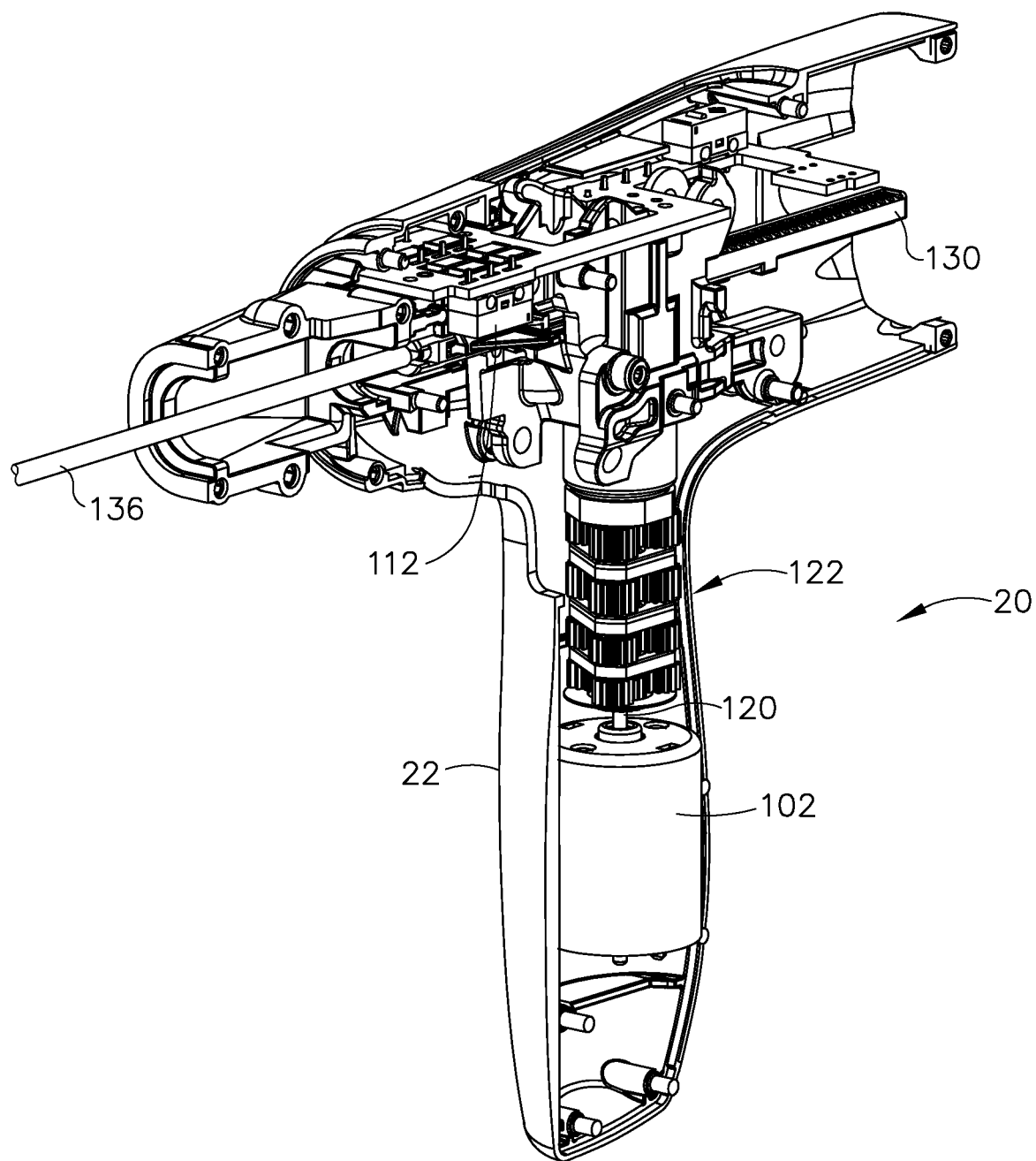
FIG. 10 depicts a perspective view of the handle assembly of the instrument of FIG. 1, with a housing half and some internal components removed.
Figure 11:
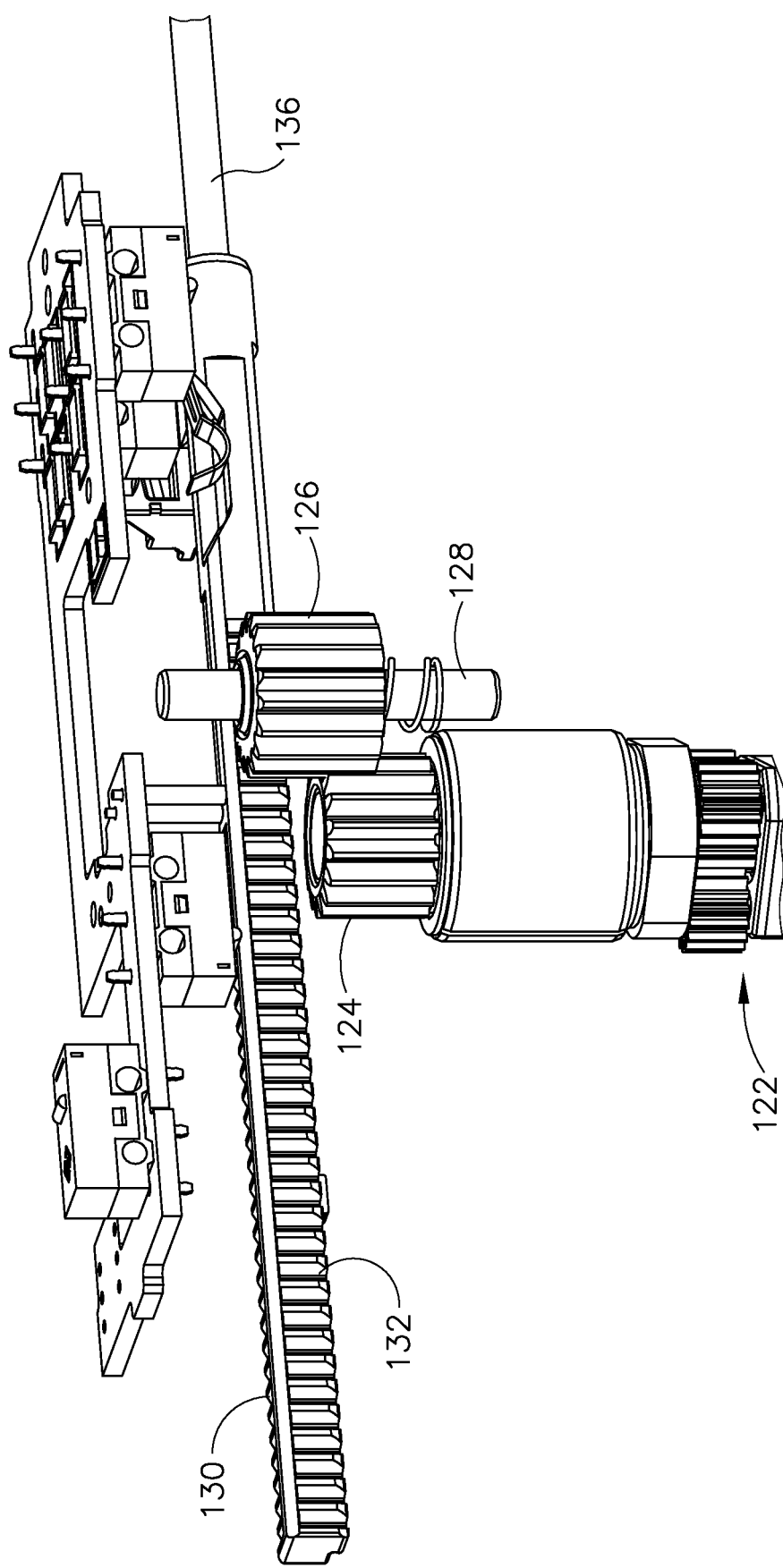
FIG. 11 depicts a perspective view of drive assembly components from the handle assembly of FIG. 10.

FIG. 10 shows motor (102) positioned within pistol grip (22) of handle assembly (20). Alternatively, motor (102) may be positioned elsewhere within handle assembly (20). Motor (102) has a drive shaft (120) that is coupled with a gear assembly (122). Thus, when motor (102) is activated, drive shaft (120) actuates gear assembly (122). As shown in FIG. 11, gear assembly (122) is in communication with a drive gear (124), which meshes with an idler pinion (126). Pinion (126) is disposed on a shaft (128) that is supported within handle assembly (20) and that is oriented parallel to drive shaft (120) of motor (102). Pinion (126) is further engaged with a rack member (130). In particular, pinion (126) meshes with teeth (132) at the proximal end of rack member (130). Rack member (130) is slidably supported in handle assembly (20). It should be understood from the foregoing that, when motor (102) is activated, the corresponding rotation of drive shaft (120) is communicated to pinion (126) via gear assembly (122), and the corresponding rotation of pinion (126) is converted to translation of rack member (130) by teeth (132). As shown in FIGS. 10-12, an elongate member (136) extends distally from rack member (130). As shown in FIG. 12, a coupling member (138) joins firing beam (82) with elongate member (136). Rack member (130), elongate member (136), coupling member (138), firing beam (82), and knife member (80) all translate together relative to handle assembly (20) in response to activation of motor (102). In other words, activation of motor (102) ultimately causes firing beam (82) to translate longitudinally, the direction of such translation depending on the direction of rotation of drive shaft (120).

It should be understood that a distal portion of elongate member (136), coupling member (138), and firing beam (82) extend through shaft assembly (130). A portion of firing beam (82) also extends through articulation section (34). In some versions, rack member (130), elongate member (136), and coupling member (138) are all substantially straight and rigid; while firing beam (82) has sufficient flexibility to bend at articulation section (34) and translate longitudinally through articulation section (34) when articulation section (34) is in a bent or articulated state.

In addition to or in lieu of the foregoing, the features operable to drive firing beam (82) may be configured in accordance with at least some of the teachings of U.S. Pat. No. 8,453,914, the disclosure of which is incorporated by reference herein. Other suitable components, features, and configurations for providing motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be actuated in accordance with at least some of the teachings of any other reference cited herein.

Figure 8:
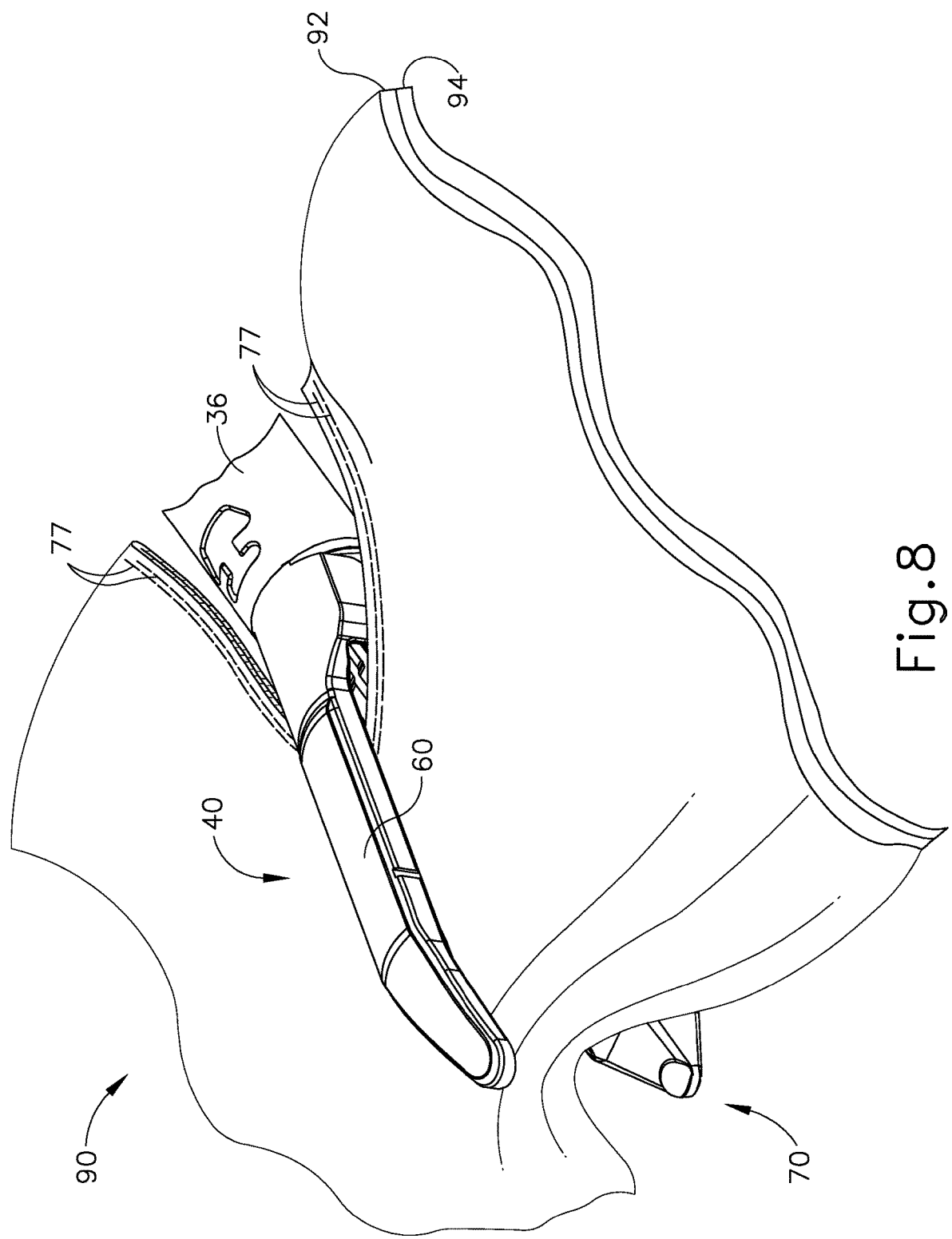
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may sever tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Shaft Assembly

FIGS. 13-20 show components of an exemplary alternative shaft assembly (200) that may be readily incorporated into instrument (10) in place of shaft assembly (30). Shaft assembly (200) is substantially identical to shaft assembly (30) except for the differences noted below. Shaft assembly (200) provides articulation and selective locking of articulation angles, as will be described in greater detail below. Shaft assembly (200) of the present example comprises a rotation knob (213), and articulation control knob (214), and an end effector (212). Rotation knob (213) is operable to rotate the entire shaft assembly (200) and end effector (212) relative to handle assembly (20) about the longitudinal axis (LA) of shaft assembly (200). This may be useful in positioning end effector (212) at a desired angular orientation about the longitudinal axis (LA) to achieve a desired positioning in relation to target tissue. In some versions, rotation knob (213) is operable to selectively lock the angular position of shaft assembly (200) and end effector (212) relative to handle assembly (20) about the longitudinal axis (LA) of shaft assembly (200). For instance, rotation knob (213) may be translatable between a first longitudinal position, in which shaft assembly (200) and end effector (212) are rotatable relative to handle assembly (20) about the longitudinal axis (LA) of shaft assembly (200); and a second longitudinal position, in which shaft assembly (200) and end effector (212) are not rotatable relative to handle assembly (20) about the longitudinal axis (LA) of shaft assembly (200).

Articulation control knob (214) is partially contained within an articulation knob casing (215). Casing (215) leads to an elongate closure tube (232). Shaft assembly (200) also comprises an end effector (212) positioned distally in relation to closure tube (232). End effector (212) includes an articulation joint (211) which allows end effector (212) to articulate laterally as will be described in further detail below. End effector (212) is substantially identical to end effector (40) except as otherwise described below. It should be understood that one difference between shaft assembly (30) and shaft assembly (200) is that articulation control knob (214) is at the same angular position about the longitudinal axis (LA) of shaft assembly (200) as lower jaw (216) in shaft assembly (200). By contrast, articulation control knob (35) is at the same angular position about the longitudinal axis (LA) of shaft assembly (30) as anvil (60) in shaft assembly (30).

Figure 14B:
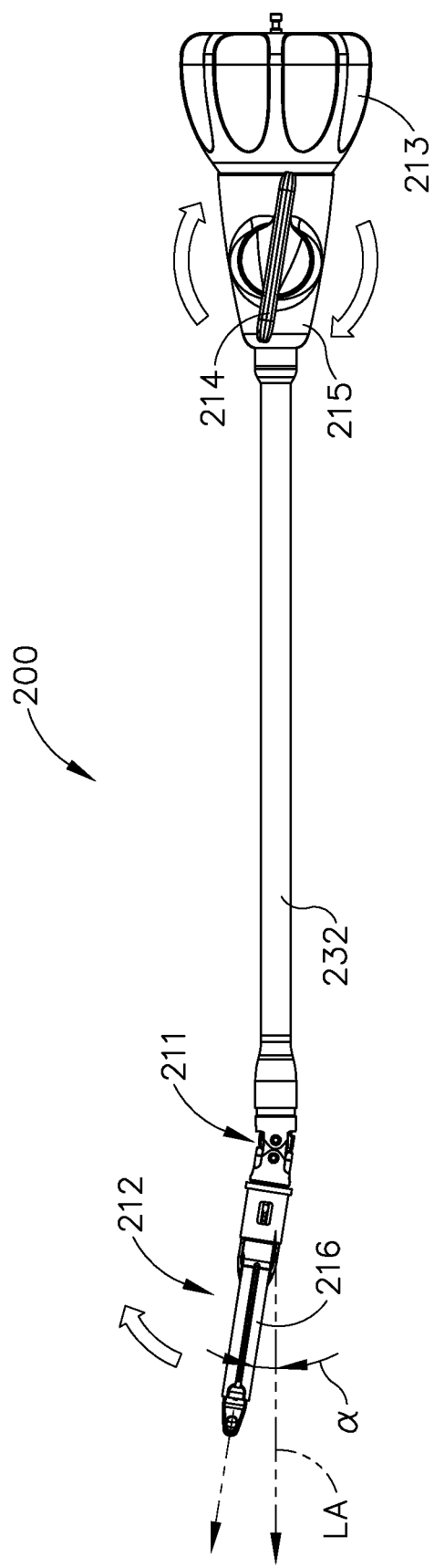
FIG. 14B depicts a top, plan view of the shaft assembly of FIG. 13 with the end effector in a second, articulated position.

FIGS. 14A-B show shaft assembly (200) and an exemplary movement of end effector (212) in response to turning of articulation control knob (214). FIG. 14A shows articulation control knob (214) in a first position where articulation control knob (214) and end effector (212) are both generally aligned along the longitudinal axis (LA) of shaft assembly (200). The user may then manually rotate articulation control knob (214) clockwise, as seen in FIG. 14B, to a second position. In response to the rotation of articulation control knob (214), end effector (212) pivots or bends at articulation joint (211) as seen in FIG. 14B to an articulation angle (α). In the illustrated version, end effector (212) articulates generally in the direction of the rotation of articulation control knob (214), though it will be understood that end effector (212) may be configured to bend in the opposite direction of the rotation of articulation control knob (214). In other words, when articulation control knob (214) is rotated clockwise, end effector (212) laterally pivots clockwise as shown in FIG. 14B; but could instead pivot counter clockwise in some other versions.

FIG. 14B shows end effector (212) laterally pivoting clockwise just slightly. It will be understood that articulation control knob (214) may be rotated further to cause end effector (212) to laterally articulate further at articulation joint (211) to any suitable angle (α). For instance, end effector (212) may pivot until an approximately 90° angle is formed across articulation joint (211). In some versions, end effector (212) may be operable to pivot even further such that end effector (212) forms an acute angle in relation to closure tube (232). Other suitable variations of end effector (212) pivoting will be apparent to one of ordinary skill in the art in view of the teachings herein. It should also be understood that articulation control knob (214) may define the same angle with the longitudinal axis (LA) as the articulation angle (α) defined between end effector (212) and the longitudinal axis (LA). Such complementary angling may provide the operator with visual feedback exterior to the patient, readily indicating the articulation angle (α) of end effector (212).

It will be appreciated that articulation control knob (214) may be rotated in the counter clockwise direction to cause end effector (212) to articulate in a counter clockwise manner. Thus, depending on the desired direction and/or amount of articulation of end effector (212), the user can simply rotate articulation control knob (214) of varying degrees in the direction that the user wishes end effector (212) to articulate to cause varying degrees of articulation of end effector (212). The mechanics of the articulation of end effector (212) will be discussed in further detail below.

Figure 15:
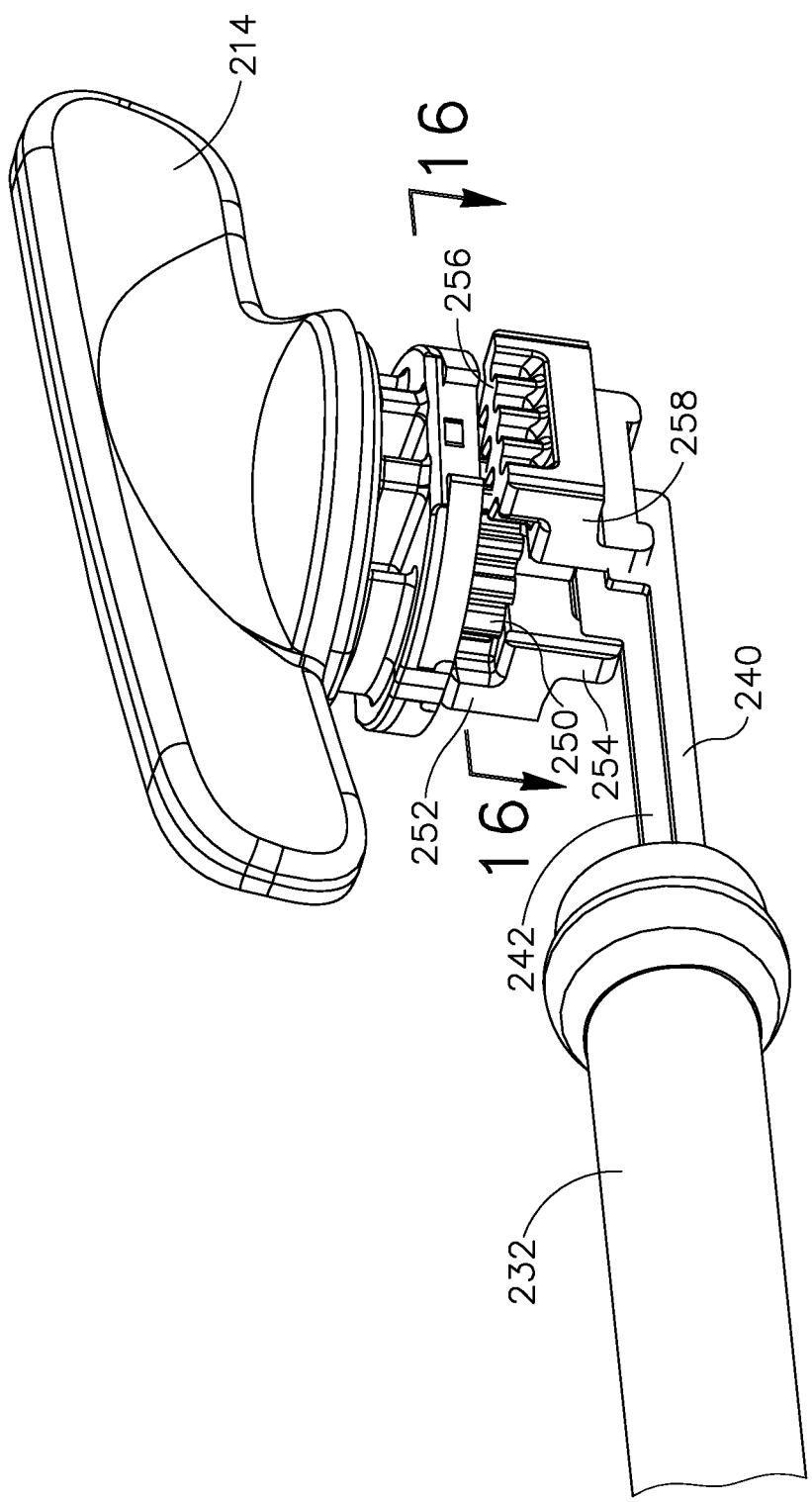
FIG. 15 depicts a perspective view of the proximal end of the shaft assembly of FIG. 13 showing the articulation knob and internal kinematic components.

FIG. 15 shows articulation control knob (214) with casing (215) removed to better show the inner workings of articulation control knob (214). Articulation control knob (214) is in communication with an articulation pinion (250). Articulation pinion (250) is in communication with a first rack (252) and a second rack (256). First rack (252) is in communication with a first arm (242) through a first intermediate block (254), whereas second rack (256) is in communication with a second arm (240) through a second intermediate block (256).

Figure 16:
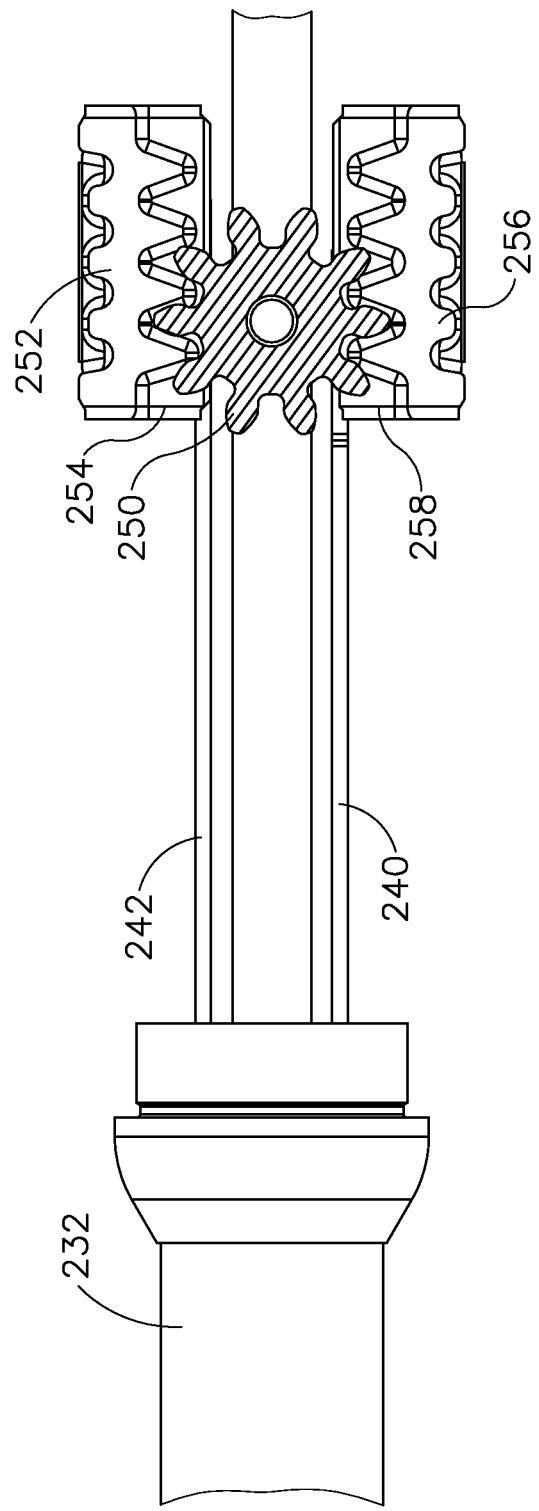
FIG. 16 depicts a top cross sectional view of the proximal end of the shaft assembly of FIG. 13 taken along the line 16-16 of FIG. 15.

Articulation control knob (214) is unitarily coupled to articulation pinion (250). As a result, when the user turns articulation control knob (214), articulation pinion (250) rotates together with articulation control knob (214). As articulation pinion (250) rotates, articulation pinion (250) translates first rack (252) and second rack (256) accordingly in opposing directions. For instance, as seen in FIG. 16, articulation pinion (250) is in communication with first rack (252) and second rack (256) such that if articulation pinion (250) rotates clockwise, first rack (252) retracts proximally away from end effector (212) whereas second rack (256) advances distally toward end effector (212). Furthermore, when articulation pinion (250) rotates counter-clockwise, first rack (252) advances distally toward end effector (212) and second rack (256) retracts proximally away from end effector (212). As first rack (252) advances and retracts, first arm (242) advances and retracts in a similar fashion. Similarly, as second rack (256) advances and retracts, second arm (240) also advances and retracts with second rack (256). Thus, rotating articulation control knob (214), which is connected to articulation pinion (250), causes first arm (242) and second arm (240) to move back and forth with first rack (252) and second rack (256). Movement of first arm (242) and second arm (240) causes movement of other components in end effector (212), which will be discussed in further detail below.

Figure 17:
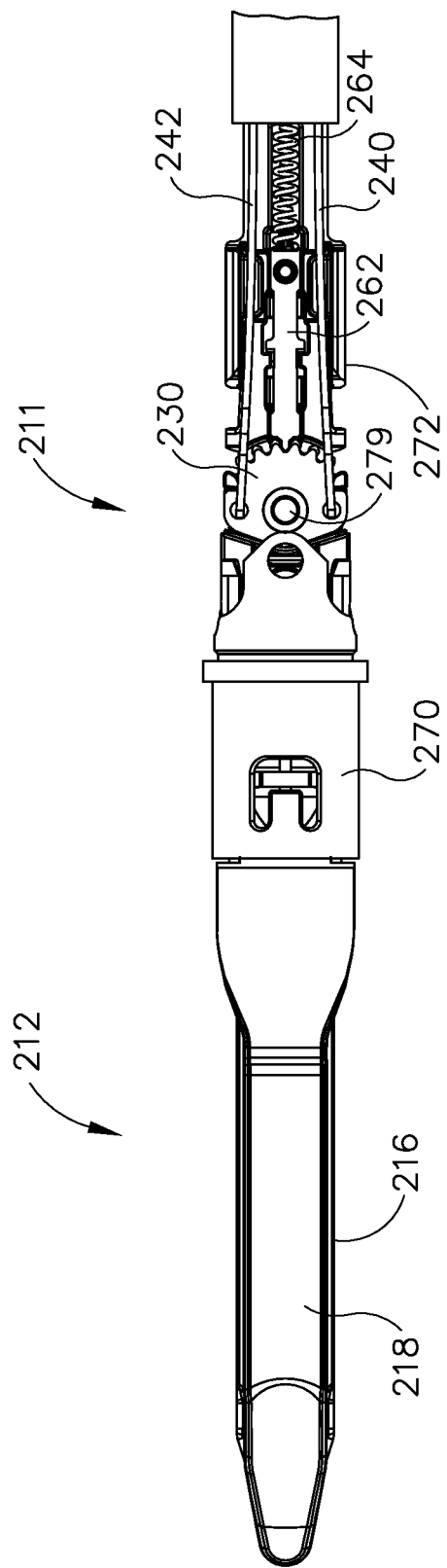
FIG. 17 depicts a top, plan view of the shaft assembly of FIG. 13 in a neutral position.

FIG. 17 shows a larger view of end effector (212), including anvil (218). First arm (242) and second arm (240) are in communication with a first cam member (230). As a result, advancing and retracting first arm (242) and second arm (240) causes first cam member (230) to rotate about a cam holding pin (279), as will be described in further detail below.

Figure 18:
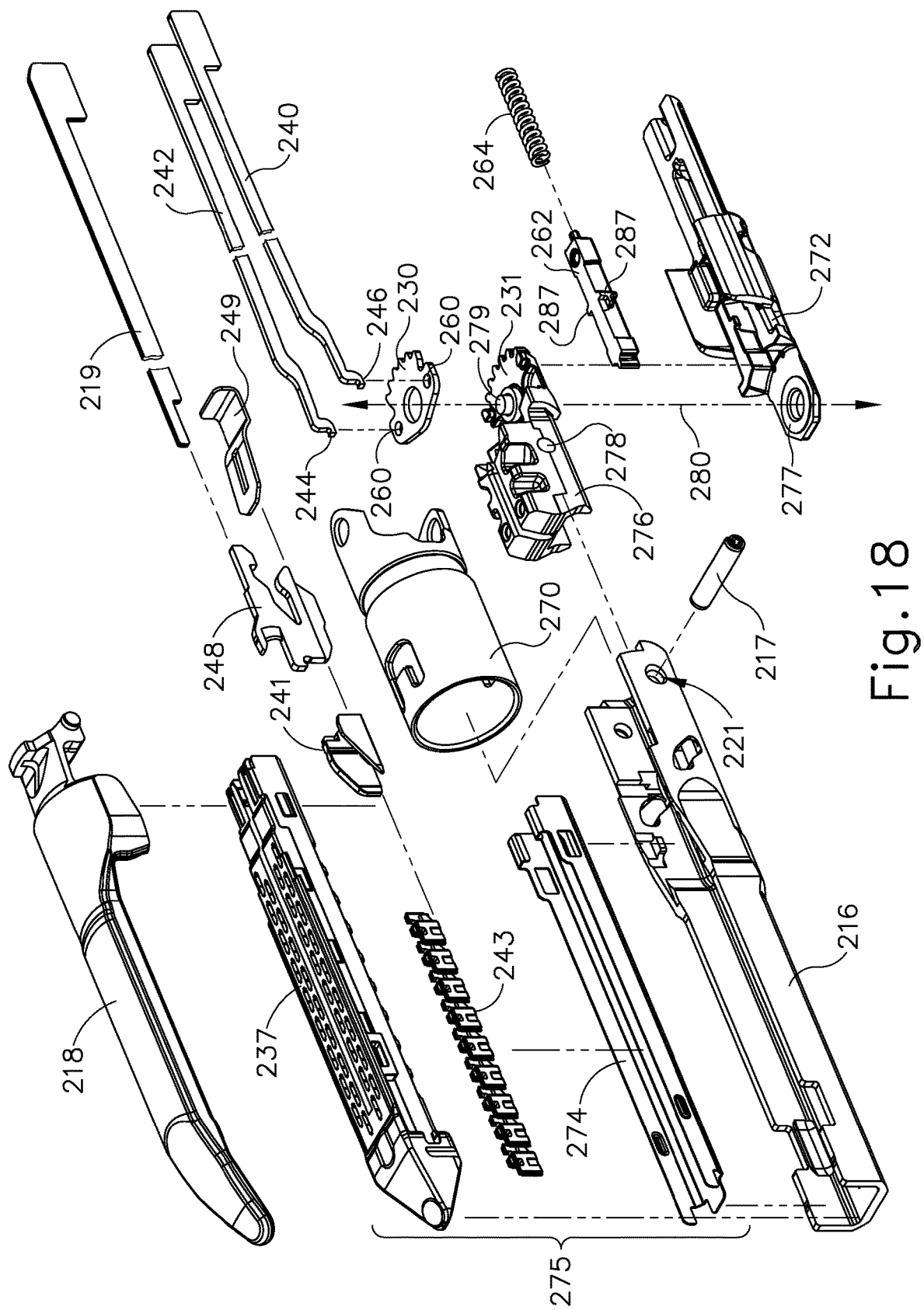
FIG. 18 depicts a perspective, exploded view of the end effector and the articulation joint of the shaft assembly of FIG. 13.

FIG. 18 shows an exploded view of end effector (212) and articulation joint (211). End effector (212) comprises an anvil (218), a lower jaw (216), and a staple cartridge (275). Cartridge (275) comprises staple drivers (243), a cartridge body (237), a tray (274), and wedge sled (241). It will be appreciated that anvil (218), lower jaw (216), tray (274), cartridge body (237), and wedge sled (241) are substantially similar to anvil (60) lower jaw (50), tray (64), cartridge (70), and wedge sled (78) shown in FIG. 5. Generally, tray (274) is removably received in lower jaw (216); and tray (274), cartridge body (237), and staple drivers (243) snap together to form staple cartridge (275). The proximal portions of anvil (218) and lower jaw (216) fit within closure ring (270), which is in communication with articulation joint (211). Anvil (218) is operable to close against cartridge body (237) in response to distal advancement of closure ring (270), such that anvil (218) and cartridge body (237) can clamp tissue. As with closure ring (36) and closure tube (32) described above, closure ring (270) may be advanced distally to close anvil (218) toward cartridge body (237) by driving closure tube (232) distally in response to pivoting of closure trigger (24) toward pistol grip (22). The clamped tissue may then be stapled and cut. In particular, after clamping tissue, wedge sled (241) is driven distally, which urges staple drivers (243) upwardly, which drives staples (not shown, but would otherwise be positioned above staple drivers (243) like staples (77) described above) through tissue and against anvil (218), anchoring the staples in tissue. Sled (241) in the illustrated version is driven by a knife member (248), which is secured to and driven by a firing beam (219). As firing beam (219) advances, knife member (248) cuts tissue while driving sled (241).

End effector (212) of the present example further comprises resilient a lockout feature (249) that is operable to cooperate with cam holding body (276) to selectively restrict advancement of knife member (248) in the absence of an unfired cartridge (275) being loaded in lower jaw (216). By way of example only, lockout feature (249) and associated components may be configured and operable in accordance with at least some of the teachings of U.S. patent application Ser. No. 13/780,082, entitled "Lockout Feature for Movable Cutting Member of Surgical Instrument," filed Feb. 28, 2013, issued as U.S. Pat. No. 9,717,497 on Aug. 1, 2017, the disclosure of which is incorporated by reference herein; and/or in accordance with at least some of the teachings of U.S. patent application Ser. No. 14/314,108, entitled "Method of Using Lockout Features for Surgical Stapler Cartridge," filed Jun. 25, 2014, issued as U.S. Pat. No. 10,335,147 on Jul. 2, 2019, the disclosure of which is incorporated by reference herein.

Figure 19A:
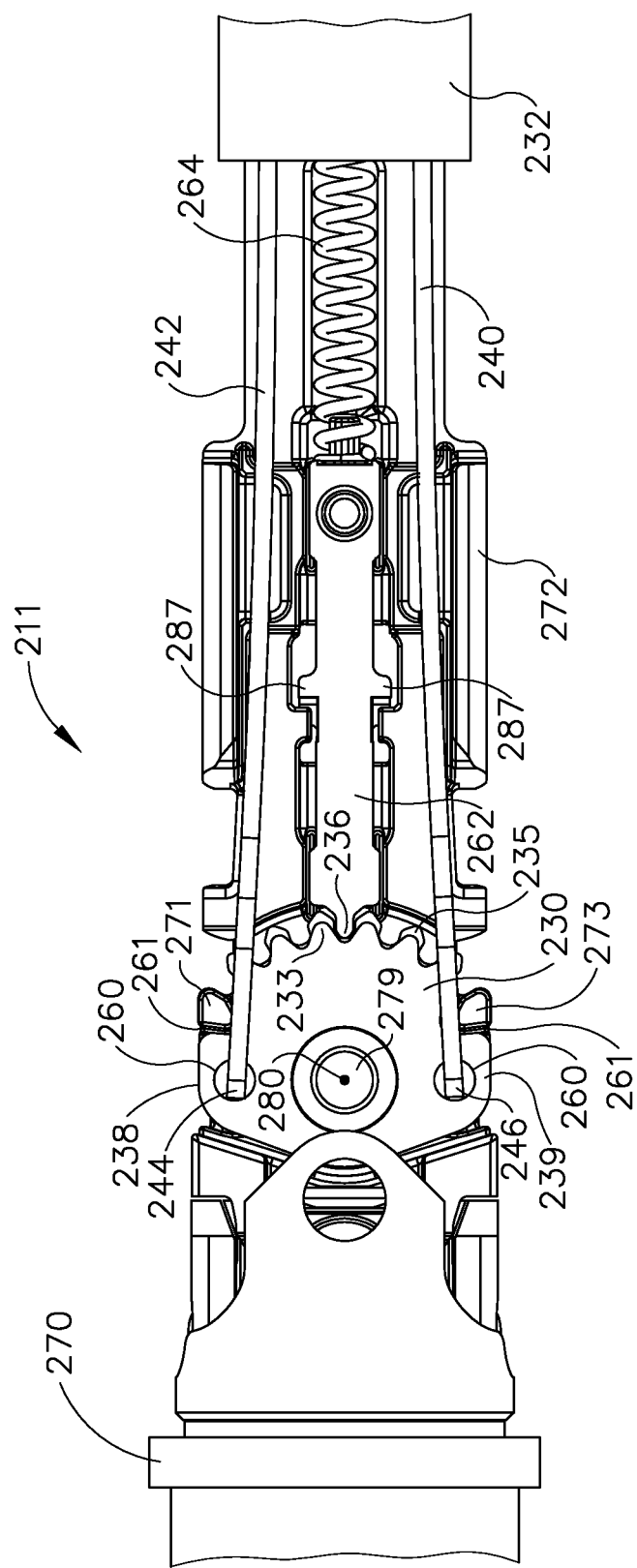
FIG. 19A depicts a top, partially internal view of the articulation joint of the shaft assembly of FIG. 13 in a first position.
Figure 19B:
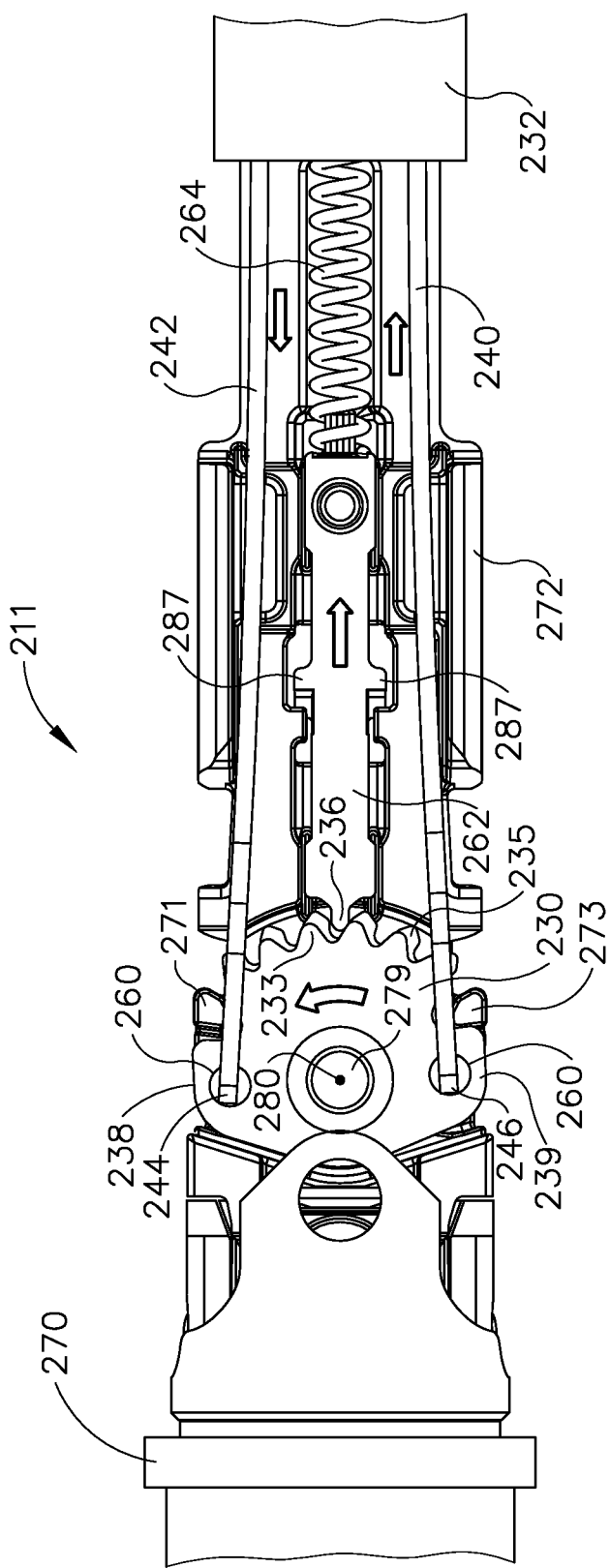
FIG. 19B depicts a top, partially internal view of the articulation joint of the shaft assembly of FIG. 13 with the first and second arms rotating a first cam member.
Figure 19C:
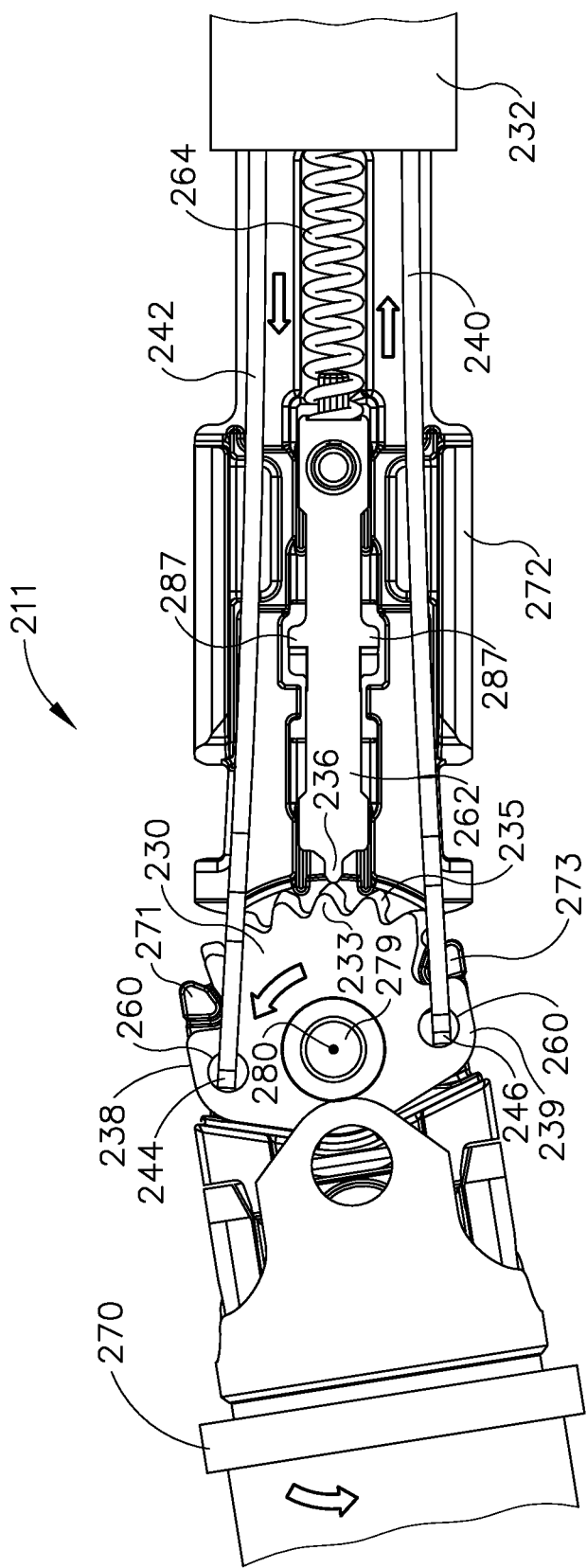
FIG. 19C depicts a top, partially internal view of the articulation joint of the shaft assembly of FIG. 13 with the first and second arms rotating a second cam member and the first cam member further.
Figure 19D:
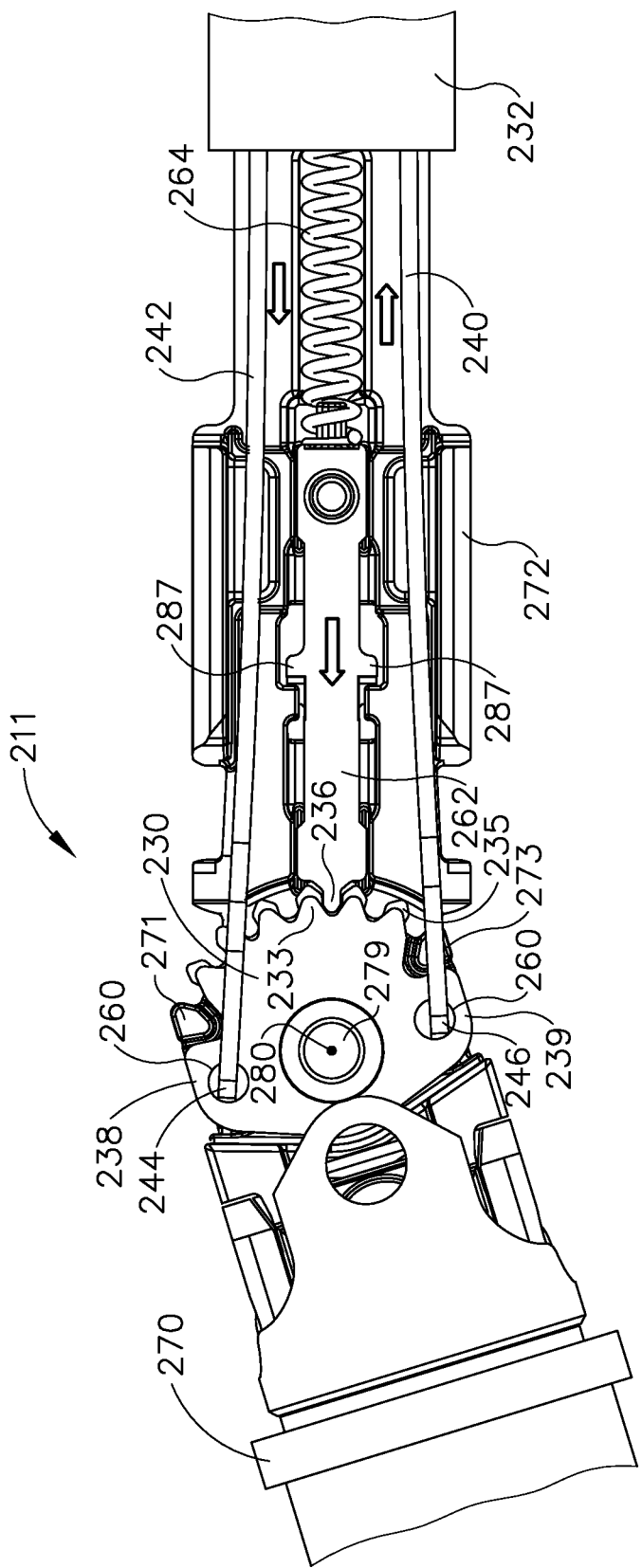
FIG. 19D depicts a top, partially internal view of the articulation joint of the shaft assembly of FIG. 13 with a lock bar resiliently positioning a lock tooth between teeth of the first cam member and the second cam member.
Figure 19E:
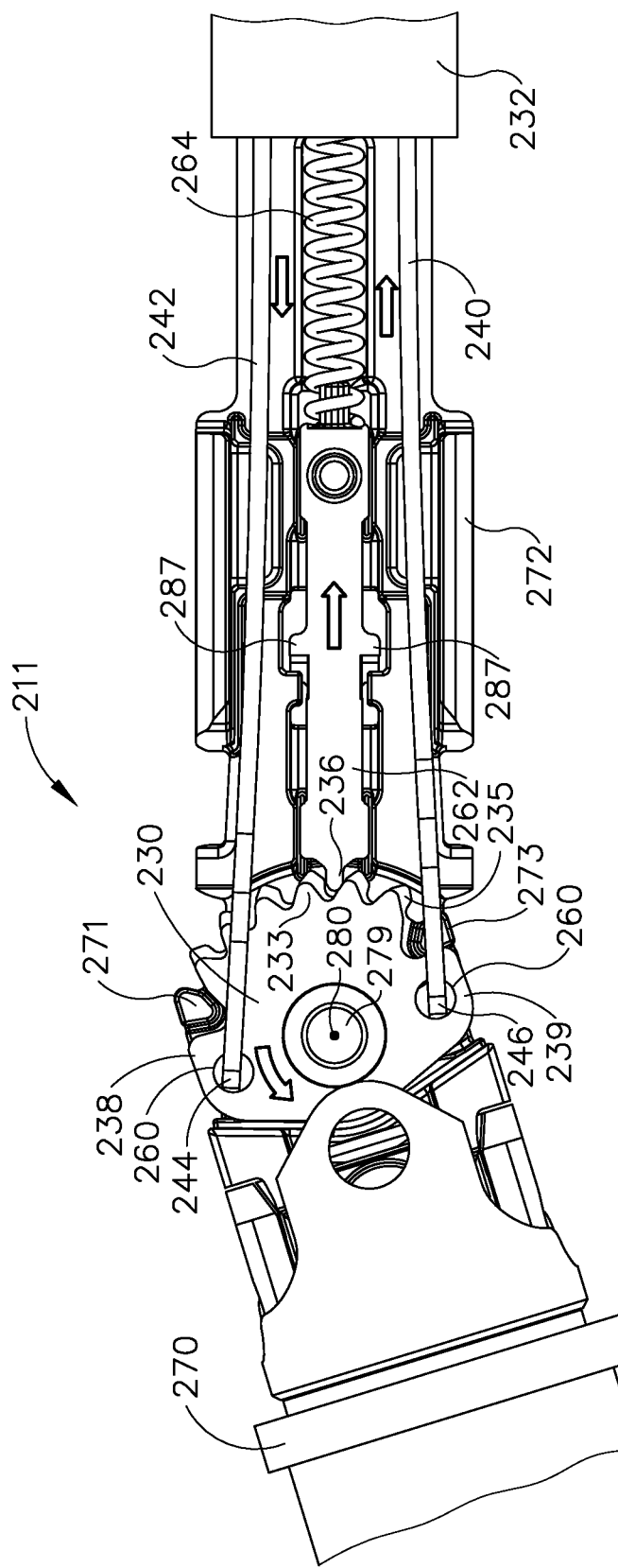
FIG. 19E depicts a top, partially internal view of the articulation joint of the shaft assembly of FIG. 13 with the first and second arms rotating the first cam member yet even further.
Figure 20:
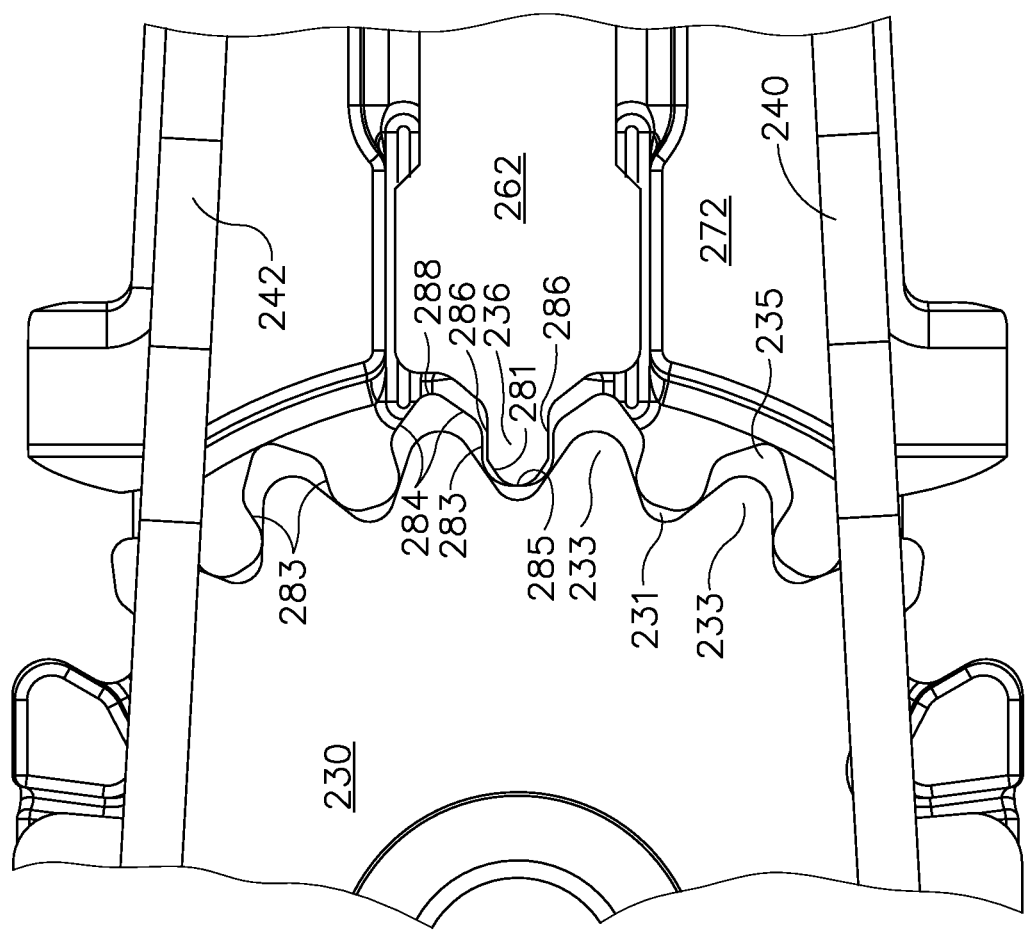
FIG. 20 depicts a plan, enlarged view of the interface of the cam members and the lock bar of the shaft assembly of FIG. 13.

As best seen in FIGS. 18-20, articulation joint (211) comprises several components that will be discussed in further detail below. Generally speaking, articulation joint (211) comprises first cam member (230), second cam member (231), cam holding body (276), a channel pin (217), joint base (272), a lock bar (262), and a spring (264). Articulation joint (211) is secured to end effector (212) via channel pin (217), which is disposed through a complementary opening (278) formed in second cam member (231) and a complementary opening (219) of lower jaw (216). End effector (212) thus pivots unitarily with second cam member (231) about a pivot axis (280) defined by cam holding pin (279), providing articulation of end effector (212), as will be described in greater detail below. Joint base (272) maintains a fixed longitudinal and angular position in shaft assembly (200), such that joint base (272) does not move relative to handle assembly (20); and such that joint base (272) provides a mechanical ground for articulation joint (211).

First arm (242) distally terminates in to a first hook (244), while second arm (240) distally terminates in a second hook (246). Hooks (244, 246) are in communication with cam openings (260) of first cam member (230). As a result, when first arm (242) advances toward end effector (212) and second arm (240) retracts, first cam member (230) rotates counter clockwise. When first arm (242) instead retracts and second arm (240) advances toward end effector (212), first cam member (230) rotates clockwise. Thus, as arms (242, 240) push and pull on cam openings (260) via hooks (244, 246), first cam member (230) rotates accordingly as just described.

First cam member (230) is stacked on a second cam member (231). Second cam member (231) and cam holding pin (279) are unitary features of cam holding body (276). In some versions, second cam member (231) may be separately constructed and fixedly coupled with cam holding body (276), such that as second cam member (231) rotates, cam holding body (276) rotates. First cam member (230) is rotationally coupled with cam holding pin (279), which is coaxially aligned with base opening (277) of joint base (272) along a pivot axis (280). Thus, first cam member (230) is rotatable about pivot axis (280), relative to second cam member (231), cam holding body (276), and joint base (272). Lock bar (262) is in selective communication with first cam member (230) and second cam member (231), which will be described further below. Lock bar (262) is further in communication with spring (264), which distally biases lock bar (262). Joint base (272) is shaped to provide a seat and/or channel for lock bar (262) to longitudinally translate relative to joint base (272). Lock bar (262) further includes a pair of bosses (287) operable to engage joint base (272) to restrict distal motion of lock bar (262).

As discussed above, actuating articulation control knob (214) causes opposing advancement and retraction of arms (242, 240). It will be understood that this motion of arms (242, 240) rotates first cam member (230) about cam holding pin (279). As a result of rotating first cam member (230), second cam member (231) rotates with cam holding body (276). Thus, articulation joint (211) articulates, thereby pivoting end effector (212) at articulation joint (211). In particular, cam holding pin (279) and base opening (274) define a pivot axis (280), which is generally perpendicular to the longitudinal axis (LA). End effector (212) pivots about pivot axis (280) in response to the rotation of first cam member (230), which drives second cam member (231) as will be discussed below. FIGS. 19A-E illustrate the details of rotating first cam member (230) to drive the articulation of end effector (212).

FIG. 19A shows articulation joint (211) in a first position. Lock bar (262) is distally biased to engage second cam member (231). In particular, the distal end of lock bar (262) comprises a lock tooth (236) that fits between first cam teeth (233) and second cam teeth (235) and abuts second cam member (231), which can be seen in further detail in FIG. 20. As a result of the distal bias provided by spring (264), lock tooth (236) acts as a positive lock and thus maintains the rotational position of second cam member (231). By maintaining the rotational position of second cam member (231), lock bar (262) maintains the angular position of end effector (212) about pivot axis (280), thereby maintaining any articulation angle (α). First cam member (230) comprises a pair of cam wings (238, 239), and cam holding body (276) comprises a pair of bosses (271, 273). Bosses (271, 273) are unitary features of second cam member (231) such that as bosses (271, 273) rotate, second cam member (231) also rotates. It will be appreciated that in the first position of FIG. 19A, cam wings (238, 239) and bosses (271, 273) define a small gap (261) therebetween. As a result, cam wings (238, 239) and bosses (271, 273) are not in contact. The interaction involving contact between cam wings (238, 239) and bosses (271, 273) will be described in further detail below with reference to FIGS. 19B-E. During a surgical operation, the user may guide shaft assembly (200) through a passageway (e.g. trocar, thoracotomy, etc.) to reach the surgical area with end effector (212) in a straightened position as shown in FIG. 19A.

FIG. 20 shows an enlarged view of lock tooth (236) in the position shown in FIG. 19A. As can be seen in the illustrated version, lock tooth (236) has generally straight parallel sides (286) that are operable to fit between first cam teeth (233) and second cam teeth (235). The distal end of lock tooth (236) has a rounded tip (285) with angled sides (281) leading to parallel sides (286). Each tooth (235) of second cam teeth (235) comprises generally straight parallel sides (283) and angled sides (284). Parallel sides (283) are operable to engage parallel sides (286) of lock tooth (236) to prevent lock tooth (236) from riding along second cam teeth (235) without assistance from first cam member (230). This engagement between at least one side (283) and at least one side (286) also prevents cam holding body (276) from rotating about pivot axis (280), thereby preventing end effector (212) from pivoting at articulation joint (211).

Once first cam member (230) rotates as shown in FIGS. 19B-C and as will be described in greater detail below, a rounded triangular tooth (233) of first cam member (230) will cam against angled sides (281), and will thereby drive lock bar (262) proximally in response to first cam (230) rotating. It should be understood that tooth (233) may have a variety of different shapes other than triangular. Lock tooth (236) moves proximally sufficiently such that angled sides (281) of lock tooth (236) can then eventually engage and ride along angled sides (284) of second cam teeth (235) as first cam member (230) continues to rotate and as second cam member (231) rotates. This provides further camming action to drive lock bar (262) proximally. Once lock tooth (236) traverses angled sides (284) of second cam teeth (235), then lock tooth (236) returns distally to a position between the next pair of first cam teeth (233) and second cam teeth (235) similar to the positioning shown in FIG. 20. For illustrative purposes, advancing lock tooth (236) between one set of first cam teeth (233) and second cam teeth (235) to an adjacent set of first cam teeth (233) and second cam teeth (235) may be considered one articulation increment. As lock tooth (236) distally advances, lock tooth (236) strikes second cam member (231) between second cam teeth (235). It will be understood that lock tooth (236) need not necessarily extend far enough to strike second cam member (231). For instance, lock tooth (236) may only extend distally such that parallel sides (283) prevent lock tooth (236) from riding along second cam member (231) without assistance from first cam teeth (233). In the illustrated version, bosses (287) engage joint base (272) to prevent further distal motion of lock bar (262).

As noted above, the operator may wish to pivot end effector (212) at articulation joint (211) to better position end effector (212) in relation to targeted tissue. FIG. 19B shows a second position for articulation joint (211) to move to in response to turning articulation control knob (214) shown in FIG. 15. In the illustrated version, the user has turned articulation control knob (214) counter clockwise, which rotates articulation pinion (250) counter clockwise as well. As articulation pinion (250) rotates counter clockwise, first rack (252) moves distally and second rack (256) moves proximally in relation to end effector (212). Accordingly, first arm (242) and second arm (240) as shown in FIG. 19B move such that first arm (242) advances toward effector (212) and second arm (240) retracts away from end effector (212). It will be appreciated that the distal portions of first arm (242) and second arm (240) of the illustrated version are not positioned parallel in relation to each other. Instead, first arm (242) and second arm (240) are obliquely angled in relation to each other, though it will be understood that first arm (242) and second arm (240) could be positioned parallel to each other.

Movement of arms (242, 240) as seen in FIG. 19B causes first cam member (230) to rotate counter clockwise about pivot axis (280). As first cam member (230) rotates, two actions occur in a generally simultaneous manner. First cam teeth (233) have a rounded triangular shape that urges lock bar (262) proximally away from end effector (212) through a camming action as a result of first cam teeth (233) engaging angled sides (281). Again, teeth (233) may have a variety of different shapes other than triangular. Spring (264) compresses to accommodate proximal motion of lock bar (262). As a result, rounded tip (285) moves proximally sufficient to traverse parallel sides (283). Additionally, cam wings (238, 239) rotate counter clockwise with first cam member (230). As a result of the rotation, cam wing (239) removes gap (261) between boss (273) and engages boss (273). Meanwhile, cam wing (238) moves rotationally away from boss (271). It will be understood that while first cam member (230) and lock bar (262) have moved in response to the movement of arms (242, 240) during the transition from the configuration shown in FIG. 19A to the configuration shown in FIG. 19B, second cam member (231) and accordingly end effector (212) have not yet moved. Thus, end effector (212) remains in a straight orientation at this stage.

FIG. 19C shows a third position of articulation joint (211). It will be understood that the user continues to rotate articulation control knob (214) in an effort to articulate end effector (212). Arms (242, 240) continue to move such that first arm (242) moves distally and second arm (240) moves proximally. Movement of arms (242, 240) continues to rotate first cam member (230), which causes cam wing (239) to rotationally move further thereby urging boss (273) to rotationally move as well. Since boss (273) is unitary with second cam member (231), second cam member (231) begins to rotate. As second cam member rotates (231), lock bar (262) moves further proximally as a result of angled sides (284) camming against angled sides (281) of lock tooth (236). Thus, lock tooth (236) rides along second cam teeth (235). Second cam member (231) rotates until tip (288) of second cam member (231) engages rounded tip (285). Second cam teeth (235) have parallel sides (283) such that angled edges (281) of lock tooth (236) can engage angled sides (284) only after first cam teeth (233) urges lock tooth (236) proximally such that rounded tip (285) traverses parallel sides (283). Prior to riding along first cam teeth (233), lock tooth (236) is generally unable to ride along second cam teeth (235) due to parallel sides (283) engaging parallel sides (286). It will further be appreciated that as lock tooth (236) rides along angled sides (284), lock tooth (236) disengages first cam teeth (233). As also seen in FIG. 19C, lock bar (262) and lock tooth (236) have moved to a proximal most position with just second cam teeth tip (288) being in contact with lock tooth (236). Also as a result of rotation of second cam member (231), cam holding body (276) and accordingly, sleeve (270), which leads to end effector (212), articulates in a counter clockwise direction.

FIG. 19D shows a fourth position for articulation region (211). Once again, it will be understood that user is continuing to rotate articulation control knob (214) in an effort to cause further articulation of end effector (212). Arms (242, 240) continue to move such that first arm (242) moves distally further and second arm (240) moves proximally further. Movement of arms (242, 240) continues to rotate first cam member (230), which causes cam wing (239) to push boss (273) rotationally further. Lock tooth (236) continues to ride along second cam teeth (235) until the distal bias caused by spring (264) urges lock bar (262) into the position shown in FIG. 19D. It will be appreciated that when lock bar (262) snaps into the position shown in FIG. 19D, an audible click or snap may be heard or felt. As a result, the user receives audible and/or tactile confirmation that lock tooth (236) has moved from between one set of cam teeth (233, 235) to another or otherwise has rotated by a single articulation increment. When in the position shown in FIG. 19D, first cam member (230) stops rotating and lock tooth (236) fits between cam teeth (233, 235). Sleeve (270) and accordingly end effector (212) stop articulating. A positive lock has formed because any rotational motion of second cam member (231) urged by transverse forces on end effector (212) would result in parallel sides (286) engaging parallel sides (283) and stopping any further rotation of second cam member (231), which locks the articulation of end effector (212). It should be understood that the transition from the configuration shown in FIG. 19A to the configuration shown in FIG. 19D represents articulation through one articulation increment, or increment of articulation motion, in which the distance is defined generally by the spaces between second cam teeth (235).

It will be understood that in the position shown in FIG. 19D, end effector (212) has articulated thereby providing the user with a shaft assembly (200) with an articulated end effector (212). It will be appreciated that the user may wish to use shaft assembly (200) in the position shown in FIG. 19D or may wish to pivot end effector (212) further by one or more additional articulation increments. In the event that the user does not rotate articulation control knob (214) further, the locking of lock tooth (236) between first cam teeth (233) and second cam teeth (235) prevents end effector (212) from pivoting to return to a straight position. Once end effector (212) has been articulated to a desired angle ($\alpha$), it will be understood that the user may actuate firing beam (213) to drive knife member (248) to cut and drive staples through tissue. For instance, knife member (248) and firing beam (213) may be in communication through, for instance, a bendable beam such that firing beam (213) can advance through any degree of pivot of articulation joint (211).

FIG. 19E shows a fifth position for articulation joint (211) in the event that the user wishes to pivot end effector (212) further. Once again, it will be understood that user continues to rotate articulation control knob (214). As a result, arms (242, 240) continue to move such that first arm (242) moves distally further and second arm (240) moves proximally further. Movement of arms (242, 240) continues to rotate first cam member (230), which causes cam wing (239) to push boss (273) rotationally. First cam member (230) and second cam member (231) move similarly as shown in FIGS. 19B-D, which causes end effector (212) to articulate further as well as lock in a more articulated position. It will be understood that the user may continue to rotate articulation control knob (214) to cause end effector (212) to pivot as far as the user desires. Furthermore, the user may rotate articulation control knob (214) in the opposite direction to cause arms (242, 240) and cam members (230, 231) to move in the opposite direction, thereby causing end effector (212) to articulate in an opposite direction.

As seen in the exemplary actuation shown in FIGS. 19A-19E, first cam member (230) is operable to unlock articulation joint (211) and pivot end effector (212) at articulation joint (211) about pivot axis (280), by transferring motion from arms (242, 240) to first cam member (230). In addition, second cam member (231) and lock bar (262) cooperate to lock articulation joint (211), to thereby lock the angle (α) of end effector (212) relative to the longitudinal axis (LA) of shaft assembly (200).

III. Exemplary Alternative Articulation Drive Features

As described above, some versions of articulation joint (211) are driven by a pair of bendable arms (240, 242) that are laterally spaced apart from each other and that translate longitudinally in an opposing fashion, with the distal ends of arms (240, 242) being coupled with articulation joint (211) at positions that are at the same longitudinal position as the pivot axis (280) of articulation joint (211) yet that are also laterally offset from the pivot axis (280). In some instances, it may be desirable to drive an articulation joint like articulation joint (211) by a pair of translatable arms that are coupled with the articulation joint at positions that are proximal to the pivot axis of the articulation joint instead of being laterally offset from the pivot axis at the same longitudinal position as the pivot axis. In addition or in the alternative, it may be desirable to drive an articulation joint like articulation joint (211) by a pair of translatable arms that are laterally adjacent to each other instead of being laterally spaced apart from each other. In addition or in the alternative, it may be desirable to drive an articulation joint like articulation joint (211) by a single translatable arm that is laterally offset from the pivot axis of the articulation joint.

Various merely illustrative examples of components and features that may be used to drive an articulation joint like articulation joint (211) are described in greater detail below. It should be understood that the following examples may be readily incorporated into instrument (10) in place of articulation joint (211). Various suitable ways in which the below described examples of articulation joints may be incorporated into instrument (10) will be apparent to those of ordinary skill in the art in view of the teachings herein.

It should also be understood that the articulation joints described below may be selectively locked and unlocked (i.e., to selectively maintain a straight or articulated position) in various ways. By way of example only, the articulation joints described below may be selectively locked and unlocked in accordance with at least some of the teachings above. In addition or in the alternative, the articulation joints described below may be selectively locked and unlocked in accordance with at least some of the teachings of U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015, the disclosure of which is incorporated by reference herein; at least some of the teachings of U.S. patent application Ser. No. 13/780,402, entitled "Surgical Instrument with Articulation Lock Having a Detenting Binary Spring," filed Feb. 28, 2013, issued as U.S. Pat. No. 9,795,379 on Oct. 24, 2017, the disclosure of which is incorporated by reference herein; and/or at least some of the teachings of U.S. patent application Ser. No. 14/314,276, entitled "Method of Unlocking Articulation Joint in Surgical Stapler," filed Jun. 25, 2014, issued as U.S. Pat. No. 10,064,620 on Sep. 4, 2018, the disclosure of which is incorporated by reference herein. Various ways in which the teachings of the above-cited references may be combined with the teachings below will be apparent to those of ordinary skill in the art in view of the teachings herein. Similarly, other suitable ways in which the articulation joints described below may be selectively locked and unlocked will be apparent to those of ordinary skill in the art in view of the teachings herein.

A. Exemplary Articulation Drive Member with Single Cam Slot

Figure 21A:
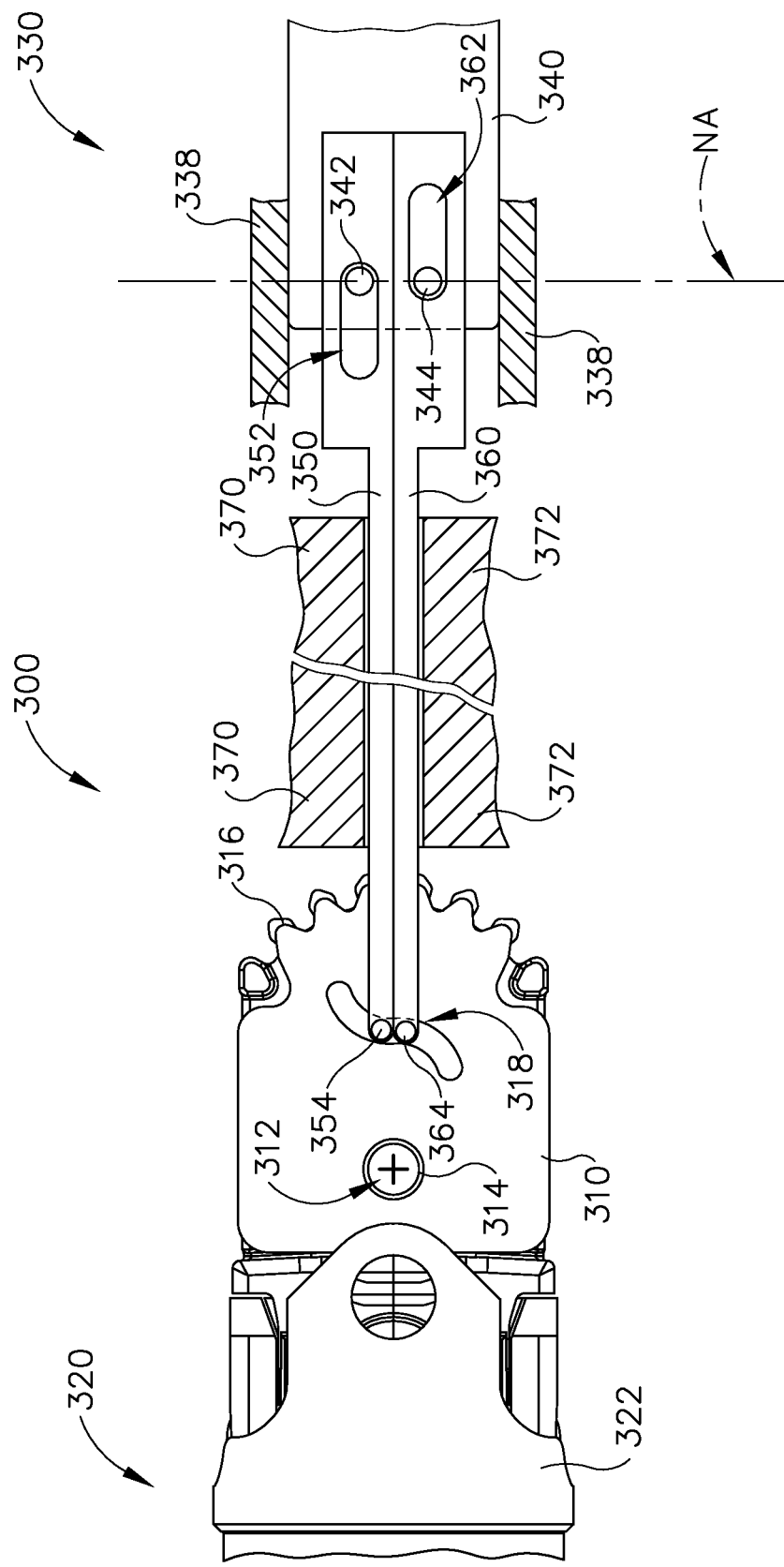
FIG. 21A depicts a partial, top plan view of exemplary alternative articulation drive features that may be incorporated into the articulation section of the shaft assembly of FIG. 13, with the articulation section in a straight configuration.
Figure 21B:
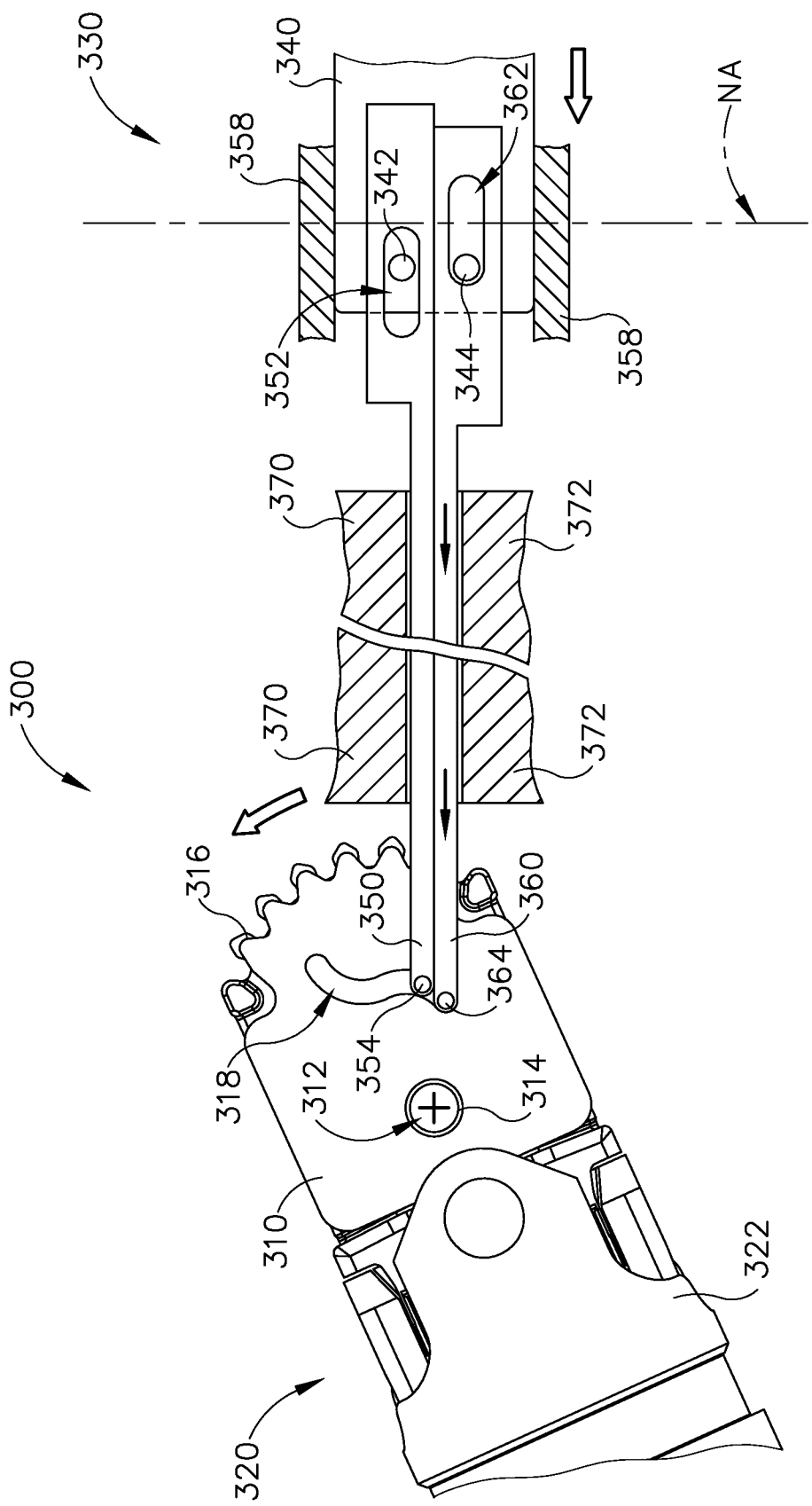
FIG. 21B depicts a partial, top plan view of the articulation drive features of FIG. 21A, with the articulation section in a first articulated configuration.
Figure 21C:
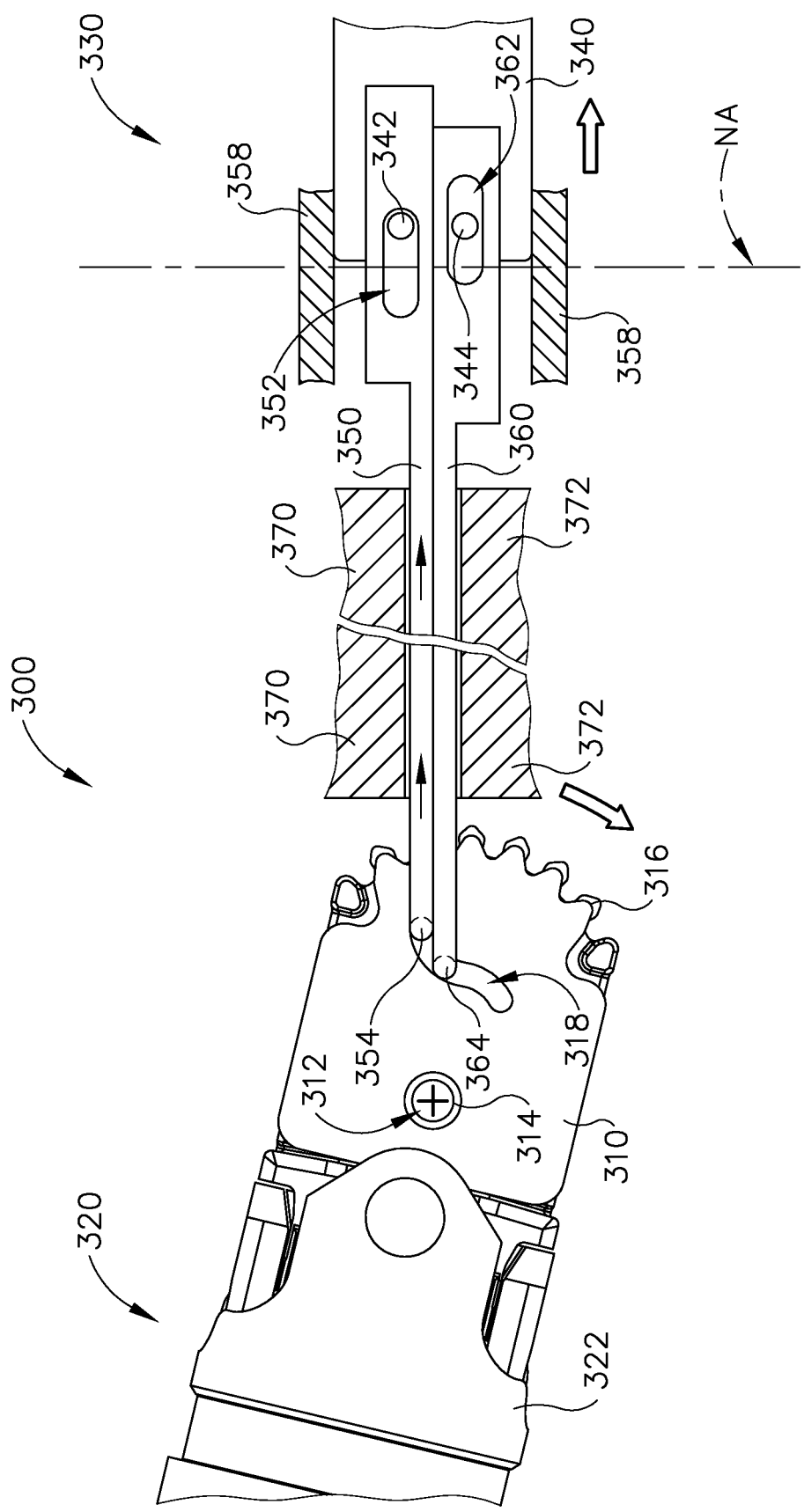
FIG. 21C depicts a partial, top plan view of the articulation drive features of FIG. 21A, with the articulation section in a second articulated configuration

FIGS. 21A-21C show an exemplary alternative articulation joint (300) that may be readily incorporated into instrument (10). Articulation joint (300) of this example comprises a cam member (310), which is pivotable about a pivot axis (312) defined by a pivot pin (314). The distal end of cam member (310) is secured to an end effector (320), such that end effector (320) will pivot with cam member (310) about pivot axis (312) to thereby laterally deflect end effector (320) away from the longitudinal axis of a shaft assembly (330), similar to the articulation shown in FIG. 14B. While FIGS. 21A-21C only show a closure sleeve (322) of end effector (320), it should be understood that end effector (320) may be configured and operable identically to end effectors (40, 212) described above. The proximal end of cam member (310) includes a plurality of proximally projecting teeth (316). Teeth (316) are similar to teeth cam teeth (235) and are thus operable to selectively engage a complementary locking member (e.g., similar to lock bar (262), etc.), to thereby selectively lock a straight or articulated orientation of cam member (310) and end effector (320) relative to shaft assembly (330). Various suitable structures and techniques that may be used to selectively lock and unlock articulation joint (300) will be apparent to those of ordinary skill in the art in view of the teachings herein.

As also shown in FIGS. 21A-21C, shaft assembly (330) of this example comprises a drive beam (340) and a closure tube (338). Drive beam (340) and closure tube (338) are each translatable relative to a handle assembly (e.g., such as handle assembly (20), etc.) or some other body; and relative to each other. While only a portion of closure tube (338) is shown, it should be understood that closure tube (338) may extend the full length of shaft assembly (330) and may be pivotally coupled with the proximal end of closure ring (322). Closure tube (338) and closure ring (322) may thus translate together relative to the handle assembly or other body, in order to selectively open and close an anvil of end effector (320) relative to a lower jaw of end effector (320). The pivotal coupling of closure tube (338) with closure ring (322) may enable closure tube (338) and closure ring (322)

to translate together even when articulation joint (300) is in an articulated state. Closure tube (338) may be longitudinally driven based on actuation of a user input, such as closure trigger (24) or some other form of user input. Drive beam (340) may also be longitudinally driven based on actuation of a user input, such as articulation control knob (214), a slider, and/or various other kinds of user input features. Various suitable features that may be used to provide independent translation of closure tube (338) and drive beam (340) will be apparent to those of ordinary skill in the art in view of the teachings herein.

The distal end of drive beam (340) includes a pair of upwardly extending integral pins (342, 344). Pins (342, 344) are laterally offset from each other but are at the same longitudinal position. Each pin (342, 344) is associated with a respective drive arm (350, 360). In particular, the proximal end of a first drive arm (350) includes an elongate slot (352) in which pin (342) is disposed. The proximal end of a second drive arm (360) includes an elongate slot (362) in which pin (344) is disposed. The distal end of first drive arm (350) includes a downwardly extending pin (354). Similarly, the distal end of second drive arm (360) includes a downwardly extending pin (364). Pins (354, 364) are both disposed in a curved slot (318) that is formed in cam member (310). Arms (350, 360) are slidably positioned adjacent to each other in this example. It should also be noted that pins (354) and curved slot (318) are located in a longitudinal region that is proximal to the longitudinal region of pivot axis (312) and pivot pin (314). A set of frame structures (370, 372) are configured to guide arms (350, 360) and keep arms (350, 360) in a parallel, adjacent relationship with each other. Frame structures (370, 372) nevertheless permit guide arms (350, 360) to translate longitudinally within the channel defined between frame structure (370) and frame structure (372). It should be understood that frame structures (370, 372) may extend through shaft assembly (330) and into articulation joint (300). By way of example only, distal portions of frame structures (370, 372) may be provided by a component that is similar to joint base (272) of articulation joint (212). Other suitable ways in which frame structures (370, 372) may be provided will be apparent to those of ordinary skill in the art in view of the teachings herein.

In operation, the state of articulation of articulation joint (300) is based on the longitudinal position of drive beam (340) relative to the other components. In particular, FIG. 21A shows drive beam (340) in a neutral longitudinal position. In this position, pins (342, 344) are positioned along a transverse neutral axis (NA), which is perpendicular to the longitudinal axis of shaft assembly (330). With drive beam (340) in the neutral longitudinal position, articulation joint (300) is in a straight, non-articulated state. In other words, end effector (320) is aligned with the longitudinal axis of shaft assembly (330). In this state, pin (342) is located in the proximal end of slot (352); while pin (344) is located in the distal end of slot (352). Also in this state, pins (354, 364) are at the same longitudinal position (albeit laterally offset from each other).

FIG. 21B shows drive beam (340) advanced to a distal position. In this position, pins (342, 344) are located distal to the neutral axis (NA). During the transition from the state shown in FIG. 21A to the state shown in FIG. 21B, pin (344) has engaged drive arm (360), driving drive arm (360) distally. However, due to the elongate configuration of slot (352), pin (342) has simply travelled distally in slot (352) without driving arm (350) distally. Drive beam (340) thus drives drive arm (360) distally relative to drive arm (350) when drive beam (340) is translated distally from the neutral longitudinal position. As drive arm (360) translates distally, pin (364) travels in slot (318) of cam member (310). Due to the curved configuration of slot (318), this distal travel of pin (364) in slot (318) causes cam member (310) and end effector (320) to pivot counterclockwise about pivot axis (312). In some instances, as cam member (310) and end effector (320) pivot counterclockwise about pivot axis (312), cam member (310) will pull distally on pin (354), thereby pulling drive arm (350) distally to some degree. However, due to the distal travel of drive beam (340) during the transition from the state shown in FIG. 21A to the state shown in FIG. 21B, pin (342) may still be located within an intermediate region of slot (352), such that incidental distal movement of drive arm (350) will not result in contact between an end of slot (352) and pin (342). It should be understood from the foregoing that the articulation angle of end effector (320) may vary as a function of the distal positioning of drive beam (340). It should also be understood that various kinds of locking features may be used to selectively lock the articulated position of end effector (320). Various suitable forms that such locking features may take will be apparent to those of ordinary skill in the art in view of the teachings herein.

FIG. 21C shows drive beam (340) retracted to a proximal position. In this position, pins (342, 344) are located proximal to the neutral axis (NA). During the transition from the state shown in FIG. 21A to the state shown in FIG. 21C, pin (342) has engaged drive arm (350), driving drive arm (350) proximally. However, due to the elongate configuration of slot (362), pin (344) has simply travelled proximally in slot (362) without driving arm (360) proximally. Drive beam (340) thus drives drive arm (350) proximally relative to drive arm (360) when drive beam (340) is translated proximally from the neutral longitudinal position. As drive arm (360) translates proximally, pin (354) travels in slot (318) of cam member (310). Due to the curved configuration of slot (318), this proximal travel of pin (354) in slot (318) causes cam member (310) and end effector (320) to pivot clockwise about pivot axis (312). In some instances, as cam member (310) and end effector (320) pivot clockwise about pivot axis (312), cam member (310) will push proximally on pin (364), thereby pushing drive arm (360) proximally to some degree. However, due to the proximal travel of drive beam (340) during the transition from the state shown in FIG. 21A to the state shown in FIG. 21C, pin (344) may still be located within an intermediate region of slot (362), such that incidental proximal movement of drive arm (360) will not result in contact between an end of slot (362) and pin (344). It should be understood from the foregoing that the articulation angle of end effector (320) may vary as a function of the proximal positioning of drive beam (340). It should also be understood that various kinds of locking features may be used to selectively lock the articulated position of end effector (320). Various suitable forms that such locking features may take will be apparent to those of ordinary skill in the art in view of the teachings herein.

B. Exemplary Articulation Drive Member with Pair of Bent Cam Slots

Figure 22A:
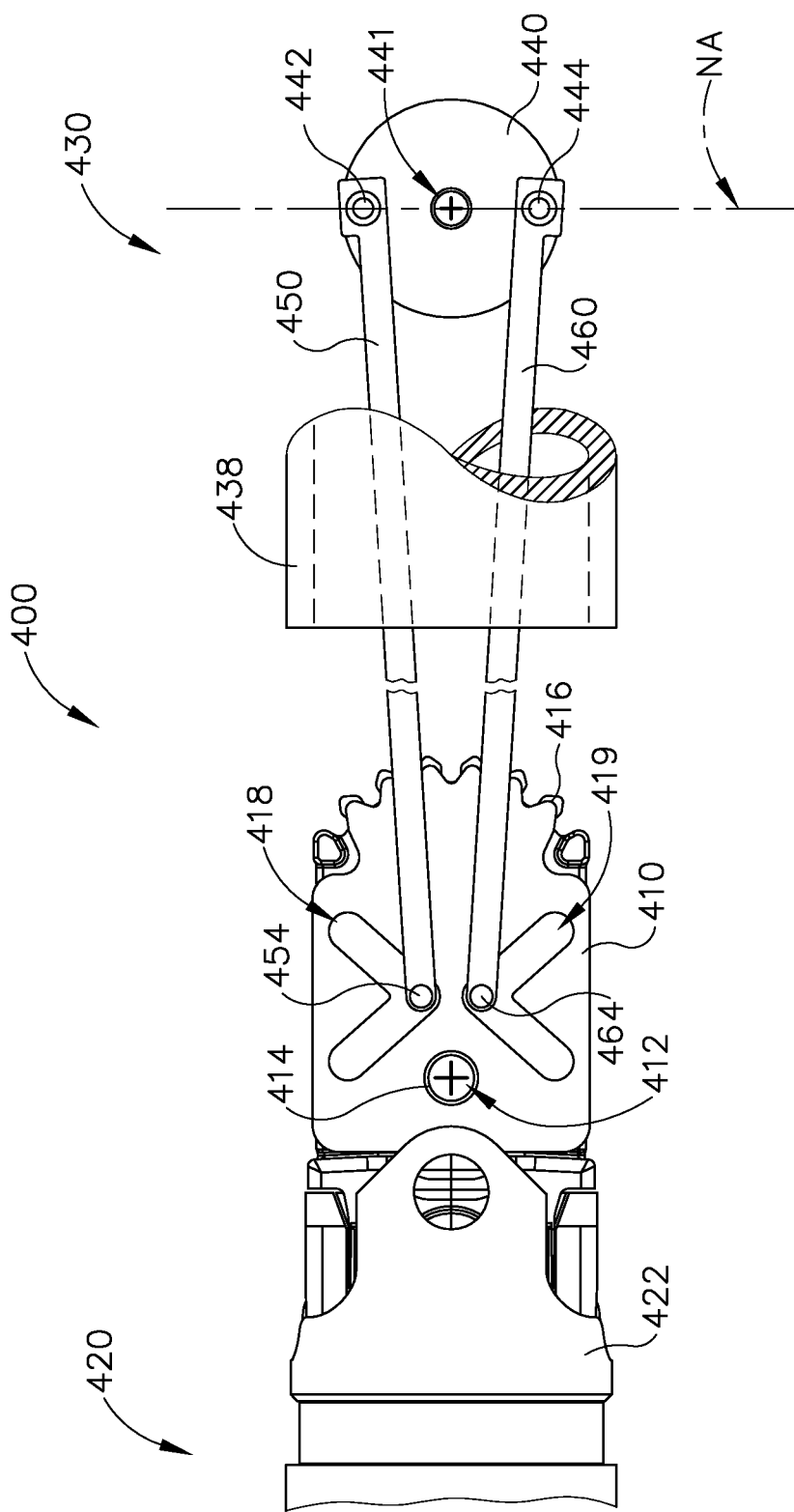
FIG. 22A depicts a partial, top plan view of other exemplary alternative articulation drive features that may be incorporated into the articulation section of the shaft assembly of FIG. 13, with the articulation section in a straight configuration.
Figure 22B:
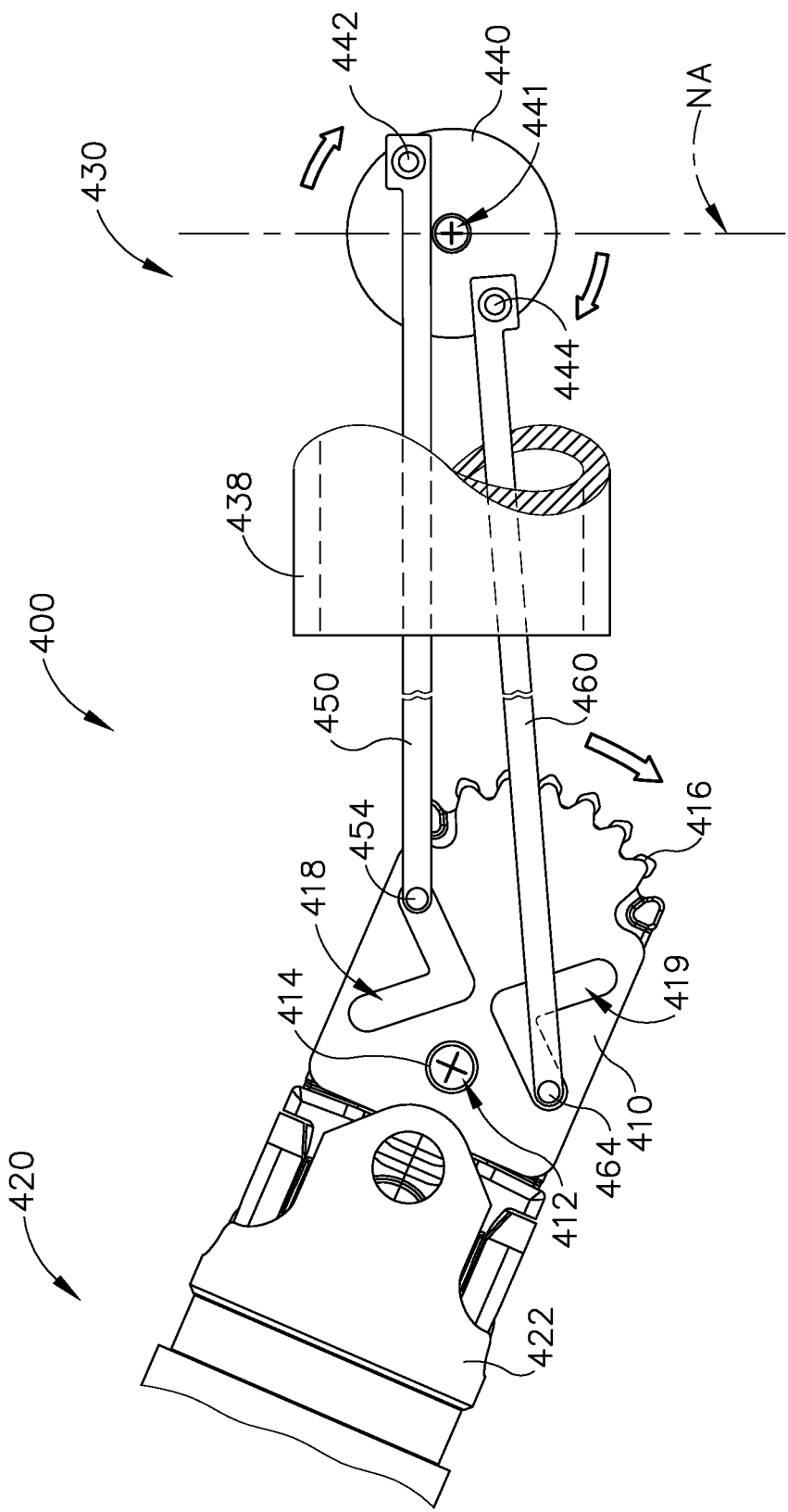
FIG. 22B depicts a partial, top plan view of the articulation drive features of FIG. 22A, with the articulation section in a first articulated configuration.

FIGS. 22A-22B show another exemplary alternative articulation joint (400) that may be readily incorporated into instrument (10). Articulation joint (400) of this example comprises a cam member (410), which is pivotable about a pivot axis (412) defined by a pivot pin (414). The distal end of cam member (410) is secured to an end effector (420), such that end effector (420) will pivot with cam member (410) about pivot axis (412) to thereby laterally deflect end effector (420) away from the longitudinal axis of a shaft assembly (430), similar to the articulation shown in FIG. 14B. While FIGS. 22A-22B only show a closure sleeve (422) of end effector (420), it should be understood that end effector (420) may be configured and operable identically to end effectors (40, 212) described above. The proximal end of cam member (410) includes a plurality of proximally projecting teeth (416). Teeth (416) are similar to teeth cam teeth (235) and are thus operable to selectively engage a complementary locking member (e.g., similar to lock bar (262), etc.), to thereby selectively lock a straight or articulated orientation of cam member (410) and end effector (420) relative to shaft assembly (430). Various suitable structures and techniques that may be used to selectively lock and unlock articulation joint (400) will be apparent to those of ordinary skill in the art in view of the teachings herein.

As also shown in FIGS. 22A-22B, shaft assembly (430) of this example comprises a rotary driver (440) and a closure tube (238). Rotary driver (440) is rotatable about an axis (441). Axis (441) is perpendicular to the longitudinal axis of shaft assembly (430) and parallel to axis pivot axis (412) of articulation joint (400). Closure tube (438) is translatable relative to a handle assembly (e.g., such as handle assembly (20), etc.) or some other body. While only a portion of closure tube (438) is shown, it should be understood that closure tube (438) may extend the full length of shaft assembly (430) and may be pivotally coupled with the proximal end of closure ring (422). Closure tube (438) and closure ring (422) may thus translate together relative to the handle assembly or other body, in order to selectively open and close an anvil of end effector (420) relative to a lower jaw of end effector (420). The pivotal coupling of closure tube (438) with closure ring (422) may enable closure tube (438) and closure ring (422) to translate together even when articulation joint (400) is in an articulated state. Closure tube (438) may be longitudinally driven based on actuation of a user input, such as closure trigger (24) or some other form of user input. Rotary driver (440) may also be longitudinally driven based on actuation of a user input, such as articulation control knob (214) and/or various other kinds of user input features. Various suitable features that may be used to provide translation of closure tube (438) and rotation of rotary driver (440) will be apparent to those of ordinary skill in the art in view of the teachings herein.

Rotary driver (440) includes a pair of upwardly extending integral pins (442, 444). Pins (442, 444) are laterally offset from each other but are at the same longitudinal position when rotary driver (440) is in the neutral angular position shown in FIG. 22A, such that pins (442, 444) are aligned with a neutral axis (NA), which is perpendicular to the longitudinal axis of shaft assembly (430). Axis (441) orthogonally intersects this neutral axis (NA) in addition to orthogonally intersecting the longitudinal axis of shaft assembly (430). Each pin (442, 444) is associated with a respective drive arm (450, 460). In particular, pin (442) is pivotably disposed within the proximal end of drive arm (450); while pin (444) is pivotably disposed within the proximal end of drive arm (460). The distal end of first drive arm (450) includes a downwardly extending pin (454). Similarly, the distal end of second drive arm (460) includes a downwardly extending pin (464). Pins (454, 464) are both disposed in respective slots (418, 419) that are formed in cam member (410). Each slot (418, 419) has a "V" shape, with the crests of the "V" shapes pointing toward each other; and with the "V" shapes opening laterally outwardly in an opposing fashion. When rotary driver (440) is in the neutral angular position shown in FIG. 22A, pins (454, 464) are both located in the crests of the "V" shapes defined by slots (418, 419). Pins (454, 464) are thus laterally offset from each other at the same longitudinal position.

In the present example at least a portion of each drive arm (450, 460) is flexible. For instance, when rotary driver (440) is in the neutral angular position shown in FIG. 22A, the proximal ends of drive arms (450, 460) bend to flare outwardly; while the distal ends of drive arms (450, 460) are straight and parallel with each other. When rotary driver (440) is rotated to a position such as that shown in FIG. 22B, the distal end of at least one arm (450, 460) bends to flare outwardly; while the proximal ends of drive arms (450, 460) are straight and parallel with each other. In some versions, the material forming drive arms (450, 460) is flexible to permit such pending. In some other versions, the material forming drive arms (450, 460) is rigid, yet each drive arm (450, 460) includes at least two segments with a hinged coupling permitting one segment to bend or pivot relative to the other segment. Other suitable ways in which drive arms (450, 460) may provide flaring or other deformation will be apparent to those of ordinary skill in the art in view of the teachings herein. It should also be understood that shaft assembly (430) and/or articulation joint (400) may include one or more frame structures (e.g., similar to frame structures (370, 372) described above) to maintain the positioning, spacing, and/or configuration of intermediate portions of drive arms (450, 460).

In operation, the state of articulation of articulation joint (400) is based on the angular position of rotary driver (440) about axis (441). In particular, FIG. 22A shows rotary driver (440) in a neutral angular position. In this position, pins (442, 444) are positioned along the transverse neutral axis (NA). With rotary driver (440) in the neutral angular position, articulation joint (400) is in a straight, non-articulated state. In other words, end effector (420) is aligned with the longitudinal axis of shaft assembly (430). In this state, pins (454, 464) are at the same longitudinal position (albeit laterally offset from each other).

FIG. 22B shows rotary driver (440) rotated clockwise from the neutral angular position. In this position, pins (442, 444) have orbited about axis (441) such that pin (442) is now located proximally in relation to the neutral axis (NA); and pin (444) is now located distally in relation to the neutral axis (NA). During the transition from the state shown in FIG. 22A to the state shown in FIG. 22B, pin (442) has pulled drive arm (450) proximally; while pin (444) has pushed drive arm (460) distally. As drive arm (450) translates proximally, pin (454) travels into the proximal portion of slot (418). As drive arm (460) translates distally, pin (464) travels distally into the distal portion of slot (419). Due to the "V" shaped configuration of slots (418, 419). The above-described motion of pins (454, 464) in corresponding slots (418, 419) causes cam member (410) and end effector (420) to pivot clockwise about pivot axis (412). To return cam member (410) and end effector (420) to the straight, neutral position, the operator may simply rotate rotary driver (440) counterclockwise from the position shown in FIG. 22B to the position shown in FIG. 22A. To drive cam member (410) and end effector (420) further counterclockwise from the position shown in FIG. 22A to a counterclockwise articulated position, the operator may rotate rotary driver (440) counterclockwise from the position shown in FIG. 22A to a position where end effector (420) has reached the desired degree of articulation.

It should be understood from the foregoing that the articulation angle of end effector (420) may vary as a function of the angular positioning rotary driver (440).

While rotary driver (440) is coupled with drive arms (450, 460) via pins (442, 444) in this example, various other kinds of couplings may be used. By way of example only, rotary driver (440) may include an integral pinion, while the proximal end of each drive arm (450, 460) may include an integral rack, such that the racks are engaged with corresponding opposite sides of the pinion. Other suitable features and relationships will be apparent to those of ordinary skill in the art in view of the teachings herein. It should also be understood that various kinds of locking features may be used to selectively lock the articulated position of end effector (420). Various suitable forms that such locking features may take will be apparent to those of ordinary skill in the art in view of the teachings herein.

C. Exemplary Articulation Drive Member with Pair of Straight Cam Slots

Figure 23A:
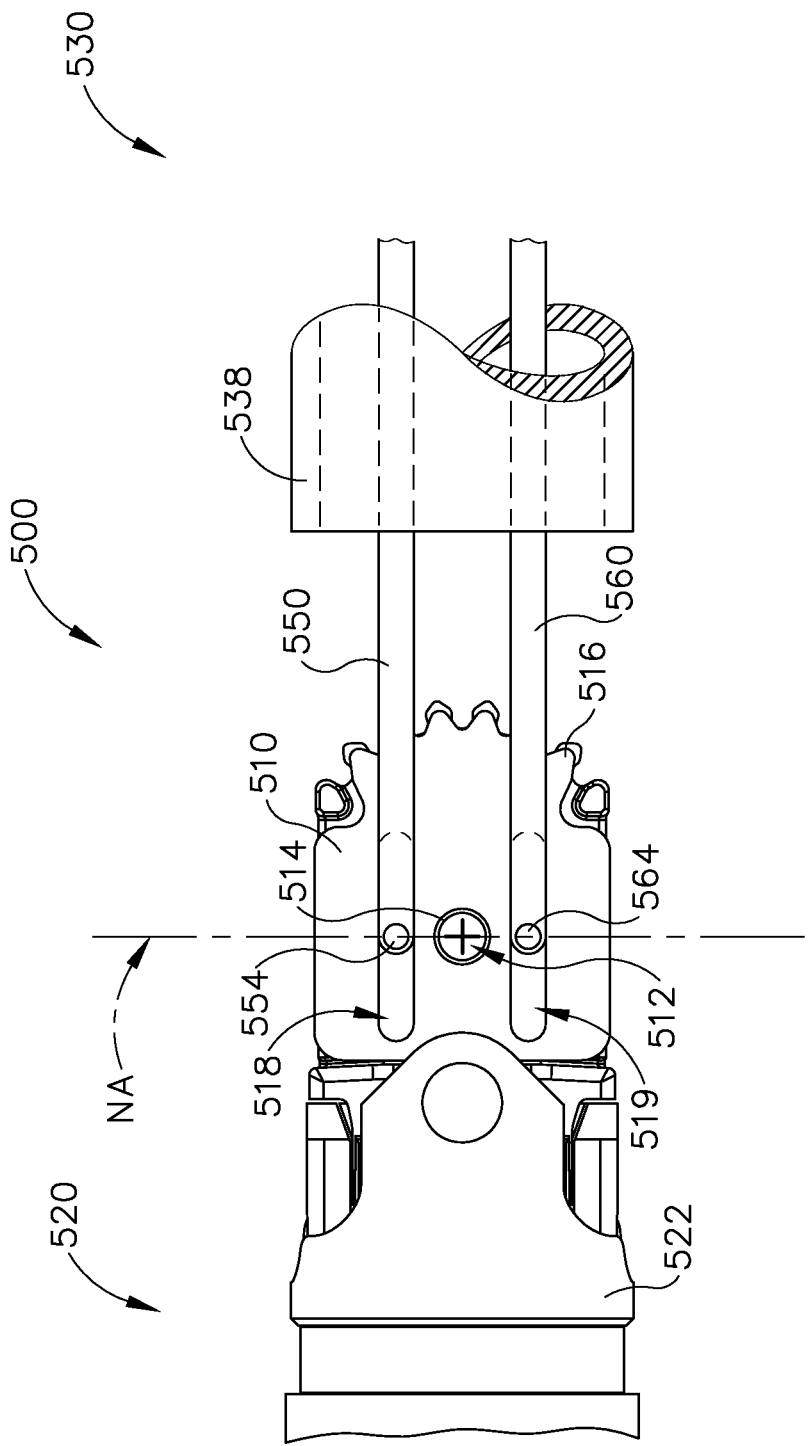
FIG. 23A depicts a partial, top plan view of other exemplary alternative articulation drive features that may be incorporated into the articulation section of the shaft assembly of FIG. 13, with the articulation section in a straight configuration.
Figure 23B:
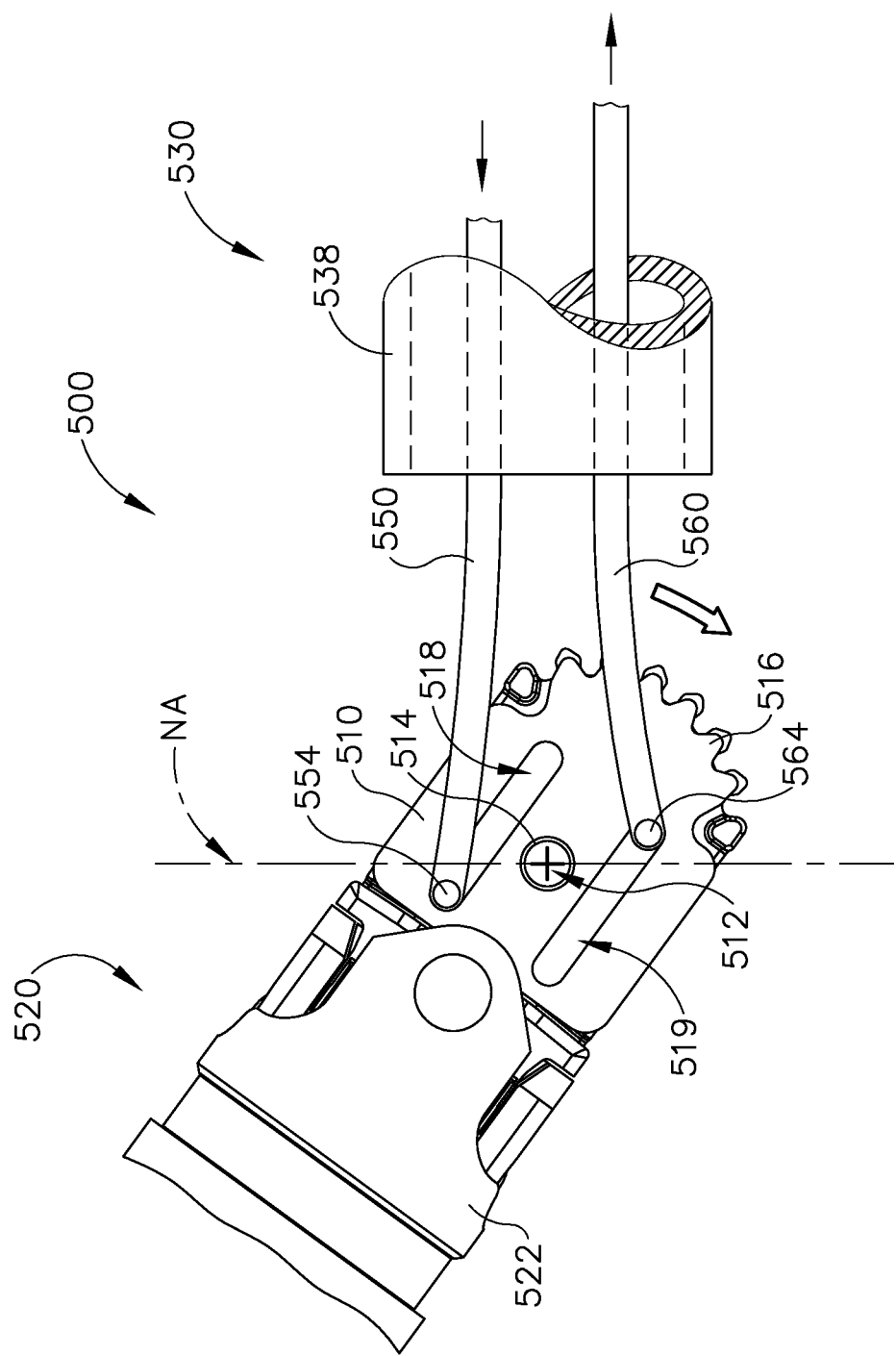
FIG. 23B depicts a partial, top plan view of the articulation drive features of FIG. 23A, with the articulation section in a first articulated configuration.

FIGS. 23A-23B show another exemplary alternative articulation joint (500) that may be readily incorporated into instrument (10). Articulation joint (500) of this example comprises a cam member (510), which is pivotable about a pivot axis (512) defined by a pivot pin (514). The distal end of cam member (510) is secured to an end effector (520), such that end effector (520) will pivot with cam member (510) about pivot axis (512) to thereby laterally deflect end effector (520) away from the longitudinal axis of a shaft assembly (530), similar to the articulation shown in FIG. 14B. While FIGS. 23A-23B only show a closure sleeve (522) of end effector (520), it should be understood that end effector (520) may be configured and operable identically to end effectors (40, 212) described above. The proximal end of cam member (510) includes a plurality of proximally projecting teeth (516). Teeth (516) are similar to teeth cam teeth (235) and are thus operable to selectively engage a complementary locking member (e.g., similar to lock bar (262), etc.), to thereby selectively lock a straight or articulated orientation of cam member (510) and end effector (520) relative to shaft assembly (530). Various suitable structures and techniques that may be used to selectively lock and unlock articulation joint (500) will be apparent to those of ordinary skill in the art in view of the teachings herein.

As also shown in FIGS. 23A-23B, shaft assembly (530) of this example comprises a closure tube (538). Closure tube (538) is translatable relative to a handle assembly (e.g., such as handle assembly (20), etc.) or some other body. While only a portion of closure tube (538) is shown, it should be understood that closure tube (538) may extend the full length of shaft assembly (530) and may be pivotally coupled with the proximal end of closure ring (522). Closure tube (538) and closure ring (522) may thus translate together relative to the handle assembly or other body, in order to selectively open and close an anvil of end effector (520) relative to a lower jaw of end effector (520). The pivotal coupling of closure tube (538) with closure ring (522) may enable closure tube (538) and closure ring (522) to translate together even when articulation joint (500) is in an articulated state. Closure tube (538) may be longitudinally driven based on actuation of a user input, such as closure trigger (24) or some other form of user input. Various suitable features that may be used to provide translation of closure tube (538) will be apparent to those of ordinary skill in the art in view of the teachings herein.

Shaft assembly (530) further includes a pair of drive arms (550, 560) within closure tube (538). Drive arms (550, 560) are operable to translate longitudinally in an opposing fashion relative to closure tube (538). Various kinds of drive actuators may be coupled with the proximal ends of drive arms to provide such opposing translation of drive arms (550, 560). By way of example only, drive arms (550, 560) may be coupled with a rotary driver similar to rotary driver (440) described above. As another merely illustrative example, the proximal end of each drive arm (550, 560) may include an integral rack, such that the racks are engaged with corresponding opposite sides of a pinion. The pinion may be manually rotatable through an input such as articulation control knob (214) and/or various other kinds of user input features. Various suitable features that may be used to provide opposing translation of drive arms (550, 560) will be apparent to those of ordinary skill in the art in view of the teachings herein.

The distal end of first drive arm (550) includes a downwardly extending pin (554). Similarly, the distal end of second drive arm (560) includes a downwardly extending pin (564). Pins (554, 564) are both disposed in respective slots (518, 519) that are formed in cam member (510). Each slot (518, 519) is straight in this example; and slots (518, 519) are parallel with each other. When the actuator that drives drive arms (550, 560) is in a neutral position, pins (554, 564) and pivot axis (564) are all located at the same longitudinal position, along a transversely extending neutral axis (NA), at positions that are laterally offset from each other. Each pin (554, 564) is also located in the longitudinally central position of the corresponding slot (518, 519). The neutral axis (NA) is perpendicular to the longitudinal axis of shaft assembly (530).

In the present example at least a distal portion of each drive arm (550, 560) is flexible. For instance, while the distal portions of drive arms (550, 560) are straight when end effector (520) is in the straight position shown in FIG. 23A, the distal portions of drive arms (550, 560) bend to flare outwardly when end effector (520) is in the articulated position shown in FIG. 23B. In some versions, the material forming drive arms (550, 560) is flexible to permit such pending. In some other versions, the material forming drive arms (550, 560) is rigid, yet each drive arm (550, 560) includes at least two segments with a hinged coupling permitting one segment to bend or pivot relative to the other segment. Other suitable ways in which drive arms (550, 560) may provide flaring or other deformation will be apparent to those of ordinary skill in the art in view of the teachings herein. It should also be understood that shaft assembly (530) and/or articulation joint (500) may include one or more frame structures (e.g., similar to frame structures (370, 372) described above) to maintain the positioning, spacing, and/or configuration of other portions of drive arms (550, 560).

In operation, the state of articulation of articulation joint (500) is based on the relative longitudinal positioning of drive arms (550, 560). In particular, FIG. 23A shows drive arms (550, 560) in a neutral position where pins (554, 564) are positioned along the same transverse neutral axis (NA), which is perpendicular to the longitudinal axis of the shaft assembly. With drive arms (550, 560) in this neutral position, articulation joint (500) is in a straight, non-articulated state. In other words, end effector (520) is aligned with the longitudinal axis of shaft assembly (530). FIG. 23B shows drive arms (550, 560) driven such that drive arm (550) has translated distally and drive arm (560) has translated proximally. Pin (554) is now located distally in relation to the neutral axis (NA); and pin (564) is now located proximally in relation to the neutral axis (NA). Pin (554) has traveled to the distal end of slot (518); and pin (564) has traveled to the proximal end of slot (519). Once pins (554, 564) have reached the corresponding opposing ends of slots (518, 519), and drive arms (550, 560) continue to translate in an opposing fashion, further opposing translation of drive arms (550, 560) causes cam member (510) and end effector (520) to pivot clockwise about pivot axis (512). To return cam member (510) and end effector (520) to the straight, neutral position, the operator may simply actuate a drive actuator to translate drive arm (550) proximally while translating drive arm (560) distally from the position shown in FIG. 23B to the position shown in FIG. 23A. To drive cam member (510) and end effector (520) further counterclockwise from the position shown in FIG. 23A to a counterclockwise articulated position, the operator may further actuate the drive actuator to further translate drive arm (550) proximally while translating drive arm (560) distally from the position shown in FIG. 23A to a position where end effector (520) has reached the desired degree of articulation.

It should be understood from the foregoing that the articulation angle of end effector (520) may vary as a function of the relative longitudinal positioning of drive arms (550, 560). Other suitable features and relationships will be apparent to those of ordinary skill in the art in view of the teachings herein. It should also be understood that various kinds of locking features may be used to selectively lock the articulated position of end effector (520). Various suitable forms that such locking features may take will be apparent to those of ordinary skill in the art in view of the teachings herein.

D. Exemplary Articulation Drive Member with Dual Linkage

FIGS. 24A-24B show another exemplary alternative articulation joint (600) that may be readily incorporated into instrument (10). Articulation joint (600) of this example comprises a proximal member (610), a distal member (620), and a rigid link (630). The proximal end of link (630) is pivotally coupled with the distal end of proximal member (610). The distal end of link (630) is pivotally coupled with the proximal end of distal member (620). Link (630) thus provides a pivotal coupling between members (610, 620). Proximal member (610) may be fixedly secured relative to shaft assembly (200) and handle assembly (20), in a manner similar to joint base (272) described above. Distal member (620) may be secured to an end effector (212), such that end effector (212) will pivot with distal member (620), in a manner similar to second cam member (231).

A driving linkage assembly (640) extends through the shaft assembly (e.g., such as shaft assembly (200), etc.) and is operable to translate relative to the shaft assembly. Driving linkage assembly (640) comprises a proximal link (642) and a distal link (644). Proximal link (642) extends along or through proximal member (610) and is longitudinally translatable relative to proximal member (610). In the present example, proximal link (642) is laterally offset from the longitudinal axis (LA) of articulation joint (600), such that proximal link (642) extends along one lateral side of proximal member (610). Links (642, 644) are pivotally coupled together via a pin (646), which is longitudinally positioned between members (610, 620). Pin (646) is disposed at the distal end of proximal link (642) and at the proximal end of distal link (644). The distal end of distal link (644) is pivotally coupled with distal member (620) via another pin (648). This pivotal coupling between distal link (644) and distal member (620) is laterally offset from the longitudinal axis (LA) of articulation joint (600).

In operation, driving linkage assembly (640) is driven distally from the position shown in FIG. 24A to the position shown in FIG. 24B. By way of example only, driving linkage assembly (640) may be coupled with a user input feature such as a slider, trigger, rotary actuator (e.g., via a rack and pinion relationship, etc.), and/or any other kind of user input features. Various suitable kinds of user input features that may be used to drive driving linkage assembly longitudinally (640) will be apparent to those of ordinary skill in the art in view of the teachings herein. As seen in the transition from FIG. 24A to FIG. 24B, distal movement of driving linkage assembly (640) causes distal member (620) to deflect laterally away from the longitudinal axis (LA) by an articulation angle ($\alpha$). In particular, distal member (620) has pivoted clockwise. This movement is provided by a combination of link (630) maintaining a fixed longitudinal distance between members (610, 620) at the lateral midregion of members (610, 620); and distal link (644) pivoting at pin (646). It should be understood that this movement of distal member (620) will provide articulation of the end effector that is coupled with distal member (620) at the selected articulation angle ($\alpha$).

In order to return distal member (620) and the end effector from the articulated position shown in FIG. 24B to the straight position shown FIG. 24B, the operator may simply retract driving linkage assembly (640) proximally. To articulate distal member (620) and the end effector counterclockwise from the position shown in FIG. 24A, the operator may continue to retract driving linkage assembly (640) proximally. This may cause distal link (644) to pivot counterclockwise about pin (646), thereby causing distal member (620) and the end effector to pivot counterclockwise to an articulated state.

It should be understood from the foregoing that the articulation angle ($\alpha$) of distal member (620) and the end effector may vary as a function of the longitudinal position of driving linkage assembly (640). The laterally offset positioning of driving linkage assembly (640) may enable articulation joint (600) to achieve articulation angles (a) that are greater than articulation angles achievable by other articulation joints described herein (e.g., greater than 45°, and in some versions greater than 90°). Other suitable features and relationships will be apparent to those of ordinary skill in the art in view of the teachings herein. It should also be understood that various kinds of locking features may be used to selectively lock the articulated position of the end effector. Various suitable forms that such locking features may take will be apparent to those of ordinary skill in the art in view of the teachings herein.

E. Exemplary Articulation Drive Member with Single Linkage

FIGS. 25-26 show another exemplary alternative articulation joint (700) that may be readily incorporated into instrument (10). Articulation joint (700) of this example comprises a driving linkage assembly (710), a frame ground (770), and a cam member (780). Cam member (780) is pivotable about a pivot axis (782) defined by a pivot pin (784). The distal end of cam member (780) is secured to an end effector (790), such that end effector (790) will pivot with cam member (780) about pivot axis (782) to thereby laterally deflect end effector (790) away from the longitudinal axis of a shaft assembly, similar to the articulation shown in FIG. 14B. While FIG. 25 only shows a closure sleeve (792) of end effector (790), it should be understood that end effector (790) may be configured and operable identically to end effectors (40, 212) described above. The proximal end of cam member (780) includes a plurality of proximally projecting teeth (786). Teeth (786) are similar to teeth cam teeth (235) and are thus operable to selectively engage a complementary locking member (e.g., similar to lock bar (262), etc.), to thereby selectively lock a straight or articulated orientation of cam member (780) and end effector (790) relative to the shaft assembly. Various suitable structures and techniques that may be used to selectively lock and unlock articulation joint (700) will be apparent to those of ordinary skill in the art in view of the teachings herein.

Driving linkage assembly (710) extends through a shaft assembly (not shown) and translates longitudinally relative to the shaft assembly. Driving linkage assembly (710) comprises a proximal link (720), a distal link (730), and a pin (740). In the present example, proximal link (720) is longitudinally offset from the longitudinal axis of the shaft assembly, though it should be understood that proximal link (720) may be positioned along or over the longitudinal axis of the shaft assembly in some other versions. Pin (740) pivotably couples links (720, 730) together. Pin (740) is disposed at the distal end of proximal link (720) and at the proximal end of distal link (730). The distal end of distal link (730) is pivotally coupled with cam member (780) via another pin (732). This pivotal coupling between distal link (730) and cam member (780) is laterally offset from the pivot axis (782) of articulation joint (700). A transverse neutral axis, which is perpendicular to the longitudinal axis of the shaft assembly, passes through pin (732) and pivot axis (782).

As best seen in FIG. 26, pin (740) includes a central shaft section (742), an upper head (744), and a lower head (746). Central shaft section (742) passes through links (720, 730) and through an elongate slot (772) that is defined in a frame ground member (770). Frame ground member (770) is defined in the shaft assembly and is configured to maintain stationary relative to the operator during operation of an instrument incorporating articulation joint (700). By way of example only, frame ground member (770) may be provided by a modified version of joint base (272). Slot (772) is configured to allow central shaft section (742) to translate longitudinally within slot (772); yet slot (772) also prevents lateral movement of central shaft section (742) in slot (772). Lower head (746) assists in retaining pin (740) in slot (772) by preventing pin (740) from traveling upwardly along the axis of pin (740). Upper head (744) prevents pin (740) from traveling downwardly along the axis of pin (740). In the present example, the configuration of pin (740) and slot (772) ensures that proximal link (720) remains parallel with slot (772) and the longitudinal axis of the shaft assembly, including when proximal link (720) is translated longitudinally. It should also be understood that pin (740) is in the longitudinal mid-point of slot (772) in the state shown in FIG. 25. In this state, end effector (790) is in a straight, non-articulated orientation, such that end effector (790) is aligned with the longitudinal axis of the shaft assembly. In some other versions, slot (772) is replaced with a channel, recess, or other kind of guide feature configured to guide pin (740).

In operation, the state of articulation joint (400) is based on the longitudinal position of driving linkage assembly (710). Driving linkage assembly (710) may be driven distally or proximally from the position shown in FIG. 25 by actuating a user input feature. By way of example only, driving linkage assembly (710) may be coupled with a user input feature such as a slider, trigger, rotary actuator (e.g., via a rack and pinion relationship, etc.), and/or any other kind of user input features. Various suitable kinds of user input features that may be used to drive driving linkage assembly longitudinally (710) will be apparent to those of ordinary skill in the art in view of the teachings herein.

When driving linkage assembly (710) is driven distally, pin (740) travels distally in slot (772). Since cam member (780) remains in a longitudinally fixed position, this distal movement of pin (740) causes distal link (730) to pivot about pin (740), which further causes cam member (780) to pivot counterclockwise about pivot axis (782). Thus, end effector (790) is rotated counterclockwise about pivot axis (782) to reach an articulated position in response to distal translation of driving linkage assembly (710). When driving linkage assembly (710) is driven proximally, pin (740) travels proximally in slot (772). Since cam member (780) remains in a longitudinally fixed position, this proximal movement of pin (740) causes distal link (730) to pivot about pin (740), which further causes cam member (780) to pivot clockwise about pivot axis (782). Thus, end effector (790) is rotated clockwise about pivot axis (782) to reach an articulated position in response to proximal translation of driving linkage assembly (710).

It should be understood from the foregoing that the articulation angle of cam member (780) and end effector (790) may vary as a function of the longitudinal position of driving linkage assembly (710). While just one driving linkage assembly (710) is provided in the present example, other variations may include two driving linkage assemblies (710). For instance, such driving linkage assemblies (710) may be provided on laterally opposite sides of the longitudinal axis of the shaft assembly; and the driving linkage assemblies (710) may be driven longitudinally in an opposing fashion as described herein in order to drive articulation of end effector (790). In some versions, arms (240, 242) of articulation joint (211) are replaced with respective driving linkage assemblies (710). In other words, the bendability of arms (240, 242) may be substituted with the pivotal relationship between rigid links (720, 730). Other suitable features and relationships will be apparent to those of ordinary skill in the art in view of the teachings herein. It should also be understood that various kinds of locking features may be used to selectively lock the articulated position of end effector (700). Various suitable forms that such locking features may take will be apparent to those of ordinary skill in the art in view of the teachings herein.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
 (a) a shaft having a longitudinal axis;
 (b) an end effector, wherein the end effector is operable to staple tissue;
 (c) an articulation joint coupling the shaft with the end effector, wherein the end effector is pivotable at the articulation joint to selectively deflect the end effector away from the longitudinal axis of the shaft; and
 (d) an articulation drive assembly, wherein the articulation drive assembly is operable to pivot the end effector at the articulation joint, wherein the articulation drive assembly comprises:
  (i) a single drive actuator,
  (ii) a first drive member and a second drive member, wherein each of the first and second drive members includes a proximal end and a distal end, wherein both of the proximal ends of the first and second drive members are operatively connected to the single drive actuator, and
  (iii) a cam member secured to the end effector and defining a pivot axis about which the end effector is configured to articulate relative to the shaft, wherein the distal ends of the first and second drive members are movably coupled with the cam member such that each distal end is positionable proximal to the pivot axis,
 wherein the first and second drive members are actuatable longitudinally by the drive actuator to articulate the end effector relative to the shaft via the cam member.

2. The apparatus of claim 1, further comprising a user input feature operatively coupled with the drive actuator, wherein the drive actuator is actuatable by the user input feature.

3. The apparatus of claim 1, wherein the proximal end of the first drive member is movably coupled to the drive actuator by a first pin and the proximal end of the second drive member is movably coupled to the drive actuator by a second pin.

4. The apparatus of claim 3, wherein the distal end of the first drive member is movably coupled to the cam member by a third pin and the distal end of the second drive member is movably coupled to the cam member by a fourth pin.

5. The apparatus of claim 1, wherein the cam member includes at least one slot configured to be slidably coupled to the distal ends of the first and second drive members.

6. The apparatus of claim 5, wherein the at least one slot includes a curved slot.

7. The apparatus of claim 5, wherein the at least one slot includes a first V shaped slot having a first crest, and a second V shaped slot having a second crest, wherein the first crest faces the second crest, wherein the first drive member is coupled with the first V shaped slot and the second drive member is coupled with the second V shaped slot.

8. The apparatus of claim 5, wherein the at least one slot includes a first elongate slot and a second elongate slot that are configured to extend parallel to the longitudinal axis, wherein the first drive member is coupled with the first elongate slot and the second drive member is coupled with the second elongate slot.

9. The apparatus of claim 1, wherein the first and second drive members are flexible, wherein a portion of each of the first and second drive members is configured to deflect away from the longitudinal axis when the end effector articulates relative to the shaft.

10. The apparatus of claim 1, wherein the cam member includes a plurality of teeth facing proximally.

11. The apparatus of claim 10, further including a locking member configured to selectively engage the plurality of teeth to releasably lock the end effector in an articulated state or a non-articulated state relative to the shaft.

12. The apparatus of claim 10, wherein the cam member includes a first cam member, wherein the plurality of teeth includes a first plurality of teeth, wherein the apparatus further includes a second cam member including a second plurality of teeth facing proximally, wherein the second cam member is pivotably coupled with the first cam member about the pivot axis.

13. The apparatus of claim 1, wherein the drive actuator includes a drive beam, wherein the drive beam is configured to be longitudinally translated relative to the shaft to drive at least one of the first drive member or the second drive member to engage the cam member and thereby articulate the end effector relative to the shaft.

14. The apparatus of claim 13, wherein the first drive member includes a first slot and the second drive member includes a second slot, wherein the drive beam includes a first pin coupled with the first slot and a second pin coupled with the second slot.

15. The apparatus of claim 1, wherein the drive actuator includes a rotary driver configured to distally extend one of the first drive member or the second drive member while proximally retracting the other of the first drive member or the second drive member.

16. An apparatus comprising:
 (a) a shaft having a longitudinal axis;
 (b) an end effector, wherein the end effector is operable to staple tissue; and
 (c) an articulation assembly that operatively couples the end effector with the shaft, wherein the articulation assembly includes:
  (i) a drive actuator positioned within the shaft,
  (ii) a cam member secured to the end effector, wherein the cam member defines at least one slot and a pivot axis about which the end effector is configured to articulate relative to the shaft, wherein the at least one slot includes a proximal slot portion, wherein the proximal slot portion is positioned proximal of the pivot axis,
  (iii) a first drive arm including a proximal end and a distal end, wherein the proximal end of the first drive arm is moveably coupled to the drive actuator and the distal end of the first drive arm is slidably coupled to the at least one slot, and
  (iv) a second drive arm including a proximal end and a distal end, wherein the proximal end of the second drive arm is movably coupled to the drive actuator and the distal end of the second drive arm is slidably coupled to the at least one slot,
 wherein the drive actuator is operable to actuate at least one of the first drive arm or the second drive arm longitudinally to drive the cam member about the pivot axis and thereby articulate the end effector relative to the longitudinal axis of the shaft.

17. The apparatus of claim 16, wherein the cam member defines two slots, wherein each of the two slots is at least partially positioned proximal of the pivot axis.

18. The apparatus of claim 16, wherein the first drive arm is translatable distally to move the end effector in a first direction away from the longitudinal axis of the shaft and the second drive arm is translatable proximally to move the end effector in a second direction away from the longitudinal axis.

19. The apparatus of claim 16, wherein the first drive arm and the second drive arm are flexible, wherein the first drive arm and the second drive arm are configured to deflect when the end effector is articulated away from the longitudinal axis.

20. An apparatus comprising:
- (a) a shaft having a longitudinal axis;
- (b) an end effector, wherein the end effector is operable to staple tissue; and
- (c) an articulation assembly that operatively couples the end effector with the shaft, wherein the articulation assembly includes:
  - (i) a drive actuator positioned within the shaft,
  - (ii) a cam member secured to the end effector, wherein the cam member defines a pivot axis about which the end effector is configured to articulate relative to the shaft, wherein the cam member includes at least one slot, and
  - (iii) a pair of drive arms, wherein each of the drive arms includes a proximal end and a distal end, wherein the proximal ends of the drive arms are moveably coupled to the drive actuator, and the distal ends of the drive arms are slidably coupled to the at least one slot of the cam member such that the distal ends are configured to be positioned proximal of the pivot axis when the end effector is in a straight configuration relative to the shaft, wherein the end effector is pivotable about the pivot axis to selectively deflect to an articulated configuration relative to the shaft, wherein in the straight configuration the end effector is aligned with the longitudinal axis of the shaft and in the articulated configuration the end effector is angled relative to the longitudinal axis.

* * * * *